(12) United States Patent
Pan et al.

(10) Patent No.: US 11,387,685 B2
(45) Date of Patent: Jul. 12, 2022

(54) LOAD-INDUCED RESONANCE-SHIFT-KEYING MODULATION SCHEME FOR SIMULTANEOUS NEAR-FIELD WIRELESS POWER AND DATA TRANSMISSION THROUGH A PAIR OF INDUCTIVE COILS

(71) Applicant: The Regents of the University of California, Oakland, CA (US)

(72) Inventors: Jiacheng Pan, Los Angeles, CA (US); Asad A. Abidi, Los Angeles, CA (US); Dejan Markovic, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 183 days.

(21) Appl. No.: 16/638,452

(22) PCT Filed: Aug. 14, 2018

(86) PCT No.: PCT/US2018/046779
§ 371 (c)(1),
(2) Date: Feb. 11, 2020

(87) PCT Pub. No.: WO2019/036519
PCT Pub. Date: Feb. 21, 2019

(65) Prior Publication Data
US 2020/0220392 A1    Jul. 9, 2020

Related U.S. Application Data

(60) Provisional application No. 62/558,798, filed on Sep. 14, 2017, provisional application No. 62/545,303, filed on Aug. 14, 2017.

(51) Int. Cl.
*H02J 50/80* (2016.01)
*H02J 50/12* (2016.01)
(Continued)

(52) U.S. Cl.
CPC ............ *H02J 50/80* (2016.02); *A61B 5/0031* (2013.01); *A61B 5/686* (2013.01); *H02J 50/12* (2016.02);
(Continued)

(58) Field of Classification Search
USPC ........................................................ 320/108
See application file for complete search history.

(56) References Cited

U.S. PATENT DOCUMENTS 1,119,732 A    12/1914  Tesla
4,561,443 A    12/1985  Hogrefe et al.
(Continued)

FOREIGN PATENT DOCUMENTS

WO    2018208990 A1    11/2018
WO    2019036519 A1    2/2019

OTHER PUBLICATIONS

International Preliminary Report on Patentability for International Application No. PCT/US2018/046779, Report dated Feb. 18, 2020, dated Feb. 27, 2020, 5 Pgs.
(Continued)

*Primary Examiner* — Bryce M Aisaka
(74) *Attorney, Agent, or Firm* — KPPB LLP

(57) ABSTRACT

Biomedical implants in accordance with various embodiments of the invention can be implemented in many different ways. The implants can be configured to receive power and transmit data, both wirelessly and simultaneously. Such devices can be configured to receive power from an external source and transmit data, such as but not limited to recorded neural data and/or other biological data, to outside the body. In many cases, the data is transmitted to the device that delivers power to the implant. For example, the power and data transmission system can be implemented with a pair of transceivers. The implant transceiver can receive power
(Continued)

wirelessly though an external transceiver while simultaneously transmitting data to the external transceiver. In several embodiments, both forward (power) and reverse (data) links use the same pair of inductive coils in the transceivers, one coil mounted in the implant and the other in the external unit.

20 Claims, 21 Drawing Sheets

(51) Int. Cl.
  *A61B 5/00* (2006.01)
  *H04B 5/00* (2006.01)
(52) U.S. Cl.
  CPC ......... *H04B 5/0031* (2013.01); *H04B 5/0037* (2013.01); *H04B 5/0081* (2013.01)

(56) References Cited

U.S. PATENT DOCUMENTS

| | | | |
|---|---|---|---|
| 4,654,880 | A | 3/1987 | Sontag |
| 10,547,200 | B2 | 1/2020 | Abidi et al. |
| 11,063,637 | B2 | 7/2021 | Yousefi et al. |
| 2002/0032471 | A1 | 3/2002 | Loftin et al. |
| 2007/0132522 | A1 | 6/2007 | Lee et al. |
| 2007/0210842 | A1 | 9/2007 | Kawamoto |
| 2008/0210762 | A1* | 9/2008 | Osada ............... G06K 19/07783 235/492 |
| 2010/0036773 | A1 | 2/2010 | Bennett |
| 2010/0039092 | A1 | 2/2010 | Cordier et al. |
| 2010/0164458 | A1 | 7/2010 | Pollard |
| 2012/0071089 | A1 | 3/2012 | Charrat et al. |
| 2014/0015327 | A1 | 1/2014 | Keeling et al. |
| 2014/0273835 | A1 | 9/2014 | Ghovanloo et al. |
| 2015/0318932 | A1 | 11/2015 | Kerselaers et al. |
| 2016/0036244 | A1 | 2/2016 | Griffith |
| 2016/0149440 | A1 | 5/2016 | Staring et al. |
| 2017/0118543 | A1 | 4/2017 | Ha et al. |
| 2017/0155194 | A1 | 6/2017 | Kanno |
| 2017/0353048 | A1 | 12/2017 | Abidi et al. |
| 2018/0366984 | A1* | 12/2018 | Joye ........................ H02J 50/80 |
| 2020/0186201 | A1 | 6/2020 | Yousefi et al. |

OTHER PUBLICATIONS

International Preliminary Report on Patentability for International Application No. PCT/US2018/031902, Report dated Nov. 12, 2019, dated Nov. 21, 2019, 9 Pgs.
International Search Report and Written Opinion for International Application No. PCT/US2018/031902, Search completed Jul. 5, 2018, dated Jul. 26, 2018, 15 Pgs.
International Search Report and Written Opinion for International Application No. PCT/US2018/046779, Search completed Oct. 11, 2018, dated Oct. 26, 2018, 11 Pgs.
Ahn et al., "Wireless Power Transfer Resonance Coupling Amplification by Load-Modulation Switching Controller", IEEE Transactions on Industrial Electronics, vol. 62, No. 2, Feb. 2015, pp. 898-909.
Ahn et al., "Wireless Power Transmission With Self-Regulated Output Voltage for Biomedical Implant", IEEE Transactions on Industrial Electronics, vol. 61, Issue 5, May 2014, pp. 2225-2235.
Baker et al., "Feedback Analysis and Design of RF Power Links for Low-Power Bionic Systems", IEEE Transactions on Biomedical Circuits and Systems, vol. 1, No. 1, Mar. 2007, pp. 28-38.
Barkhausen et al., "Lehrbuch der Elektronenröhren und ihrer technischen Anwendungen", S. Hirzel Verlag Leipzig, 1964, 194 pgs.
Cannon et al., "Magnetic Resonant Coupling as a Potential Means for Wireless Power Transfer to Multiple Small Receivers", IEEE Transactions on Power Electronics, vol. 24, No. 7, Jul. 2009, pp. 1819-1825.
Cheng et al., "A 6.78MHz 6W Wireless Power Receiver with a 3-Level 1x/1/2x/0x Reconfigurable Resonant Regulating Rectifier", 2016 IEEE International Solid-State Circuits Conference, Session 21, Harvesting and Wireless Power, vol. 21.7, Feb. 3, 2016, pp. 376-378.
Cheon et al., "Circuit-Model-Based Analysis of a Wireless Energy-Transfer System via Coupled Magnetic Resonances", IEEE Transactions on Industrial Electronics, vol. 58, No. 7, Jul. 2011, pp. 2906-2914.
Cohn, "Direct-Coupled-Resonator Filters", Proceedings of the IRE, vol. 45, No. 2, Feb. 1957, pp. 187-196.
Covic et al., "Inductive Power Transfer", Proceedings of the IEEE, vol. 101, No. 6, Jun. 2013, pp. 1276-1289.
Galbraith et al., "A Wide-Band Efficient Inductive Transdennal Power and Data Link with Coupling Insensitive Gain", IEEE Transactions on Biomedical Engineering, vol. BME-34, No. 4, Apr. 1987, pp. 265-275.
Ghovanloo et al., "A wideband frequency-shift keying wireless link for inductively powered biomedical implants", IEEE Transactions on Circuits and Systems I: Regular Papers, vol. 51, Issue 12, Dec. 2004, pp. 2374-2383.
Greenhouse, "Design of Planar Rectangular Microelectronic Inductors", IEEE Transactions on Parts, Hybrids, and Packaging, vol. 10, No. 2, Jun. 1974, p. 101-109.
Ha et al., "Energy Recycling Telemetry IC With Simultaneous 11.5 mW Power and 6.78 Mb/s Backward Data Delivery Over a Single 13.56 MHz Inductive Link", IEEE Journal of Solid-State Circuits, vol. 51, Issue 11, Nov. 2016, pp. 2664-2678.
Hegazi et al., "A Filtering Technique to Lower LC Oscillator Phase Noise", IEEE Journal of Solid-State Circuits, vol. 36, Issue 12, Dec. 2001, pp. 1921-1930.
Huang et al., "A Wireless Power Transfer System with Enhanced Response and Efficiency by Fully-Integrated Fast-Tracking Wireless Constant-Idle-Time Control for Implants", Symposium on VLSI Circuits Digest of Technical Papers, Honolulu, Hawaii, Jun. 15-17, 2016, 2 pgs.
Hui, "Planar Wireless Charging Technology for Portable Electronic Products and Qi", Proceedings of the IEEE, vol. 101, No. 6, Jun. 2013, pp. 1290-1301.
Inanlou, et al., "A 10.2 Mbps Pulse Harmonic Modulation Based Transceiver for Implantable Medical Devices", IEEE Journal of Solid-State Circuits, vol. 46, Issue 6, Jun. 2011, pp. 1296-1306.
Inanlou, et al., "Wideband Near-Field Data Transmission Using Pulse Harmonic Modulation", IEEE Transactions on Circuits and Systems I: Regular Papers, vol. 58, Issue 1, Jan. 2011, pp. 186-195.
Jow et al., "Design and Optimization of Printed Spiral Coils for Efficient Transcutaneous Inductive Power Transmission", IEEE Transactions on Biomedical Circuits and Systems, vol. 1, No. 3, Sep. 2007, pp. 193-202.
Kiani et al., "A 13.56-Mbps Pulse Delay Modulation Based Transceiver for Simultaneous Near-Field Data and Power Transmission", IEEE Transactions on Biomedical Circuits and Systems, vol. 9, Issue 1, Feb. 2015, pp. 1-11.
Kiani et al., "A 20-Mb/s Pulse Harmonic Modulation Transceiver for Wideband Near-Field Data Transmission", IEEE Transactions on Circuits and Systems II: Express Briefs, vol. 60, Issue 7, Jul. 2013, pp. 382-386.
Kiani et al., "A Power-Management ASIC with Q-Modulation Capability for Efficient Inductive Power Transmission", 2015 IEEE International Solid-State Circuits Conference, Session 12, Inductor-Based Power Conversion, vol. 12.7, Feb. 24, 2015, pp. 226-228.
Kiani et al., "Design and Optimization of a 3-Coil Inductive Link for Efficient Wireless Power Transmission", IEEE Transactions on Biomedical Circuits and Systems, vol. 5, No. 6, Dec. 2011, pp. 579-591.
Kurs et al., "Wireless Power Transfer via Strongly Coupled Magnetic Resonances", Science, vol. 317, No. 5834, Jul. 6, 2007, pp. 83-86.
Lee et al., "Impedance-Matched Wireless Power Transfer Systems Using an Arbitrary Numbers of Coils With Flexible Coil Positioning", IEEE Antennas and Wireless Propagation Letters, vol. 13, Jun. 18, 2014, pp. 1207-1210.

(56) References Cited

OTHER PUBLICATIONS

Li et al., "Wireless Power Transfer System Using Primary Equalizer for Coupling- and Load-Range Extension in Bio-Implant Applications", 2015 IEEE International Solid-State Circuits Conference, Session 12, Inductor-Based Power Conversion, vol. 12.8, Feb. 24, 2015, pp. 228-230.

Lim et al., "An Adaptive Impedance-Matching Network Based on a Novel Capacitor Matrix for Wireless Power Transfer", IEEE Transactions on Power Electronics, vol. 29, No. 8, Aug. 2014, pp. 4403-4413.

Lin et al., "An Inductive Power and Data Telemetry Subsystem With Fast Transient Low Dropout Regulator for Biomedical Implants", IEEE Transactions on Biomedical Circuits and Systems, vol. 10, Issue 2, Apr. 2016, pp. 435-444.

Lo et al., "A 176-Channel 0.5cm3 0.7g Wireless Implant for Motor Function Recovery after Spinal Cord Injury", IEEE International Solid-State Circuits Conference (ISSCC), San Francisco, California, January 31-Feb. 4, 2016, 3 pgs.

Mandal et al., "Power-Efficient Impedance-Modulation Wireless Data Links for Biomedical Implants", IEEE Transactions on Biomedical Circuits and Systems, vol. 2, Issue 4, Dec. 2008, pp. 301-315.

Martin et al., "Input Admittance Characteristics of a Tuned Coupled Circuit", Proceedings of the IRE, vol. 40, No. 1, Jan. 1952, pp. 57-61.

Middlebrook, "Low-Entropy Expressions: The Key to Design-Oriented Analysis", Proceedings of the 21st Frontiers in Education Conference, Engineering Education in a New World Order, West Lafayette, Indiana, Sep. 21-24, 1991, pp. 399-403.

Middlebrook, "Null Double Injection and the Extra Element Theorem", IEEE Transactions on Education, vol. 32, No. 3, Aug. 1989, pp. 167-180.

Middlebrook, "The General Feedback Theorem: A Final Solution for Feedback Systems", IEEE Microwave Magazine, vol. 7, No. 2, Apr. 2006, pp. 50-63.

Mirzaei et al., "The Quadrature LC Oscillator: A Complete Portrait Based on Injection Locking", JSSC, 2007, vol. 42, No. 9, pp. 1916-1932.

Miura et al., "A 1Tb/s 3W inductive-coupling transceiver for inter-chip clock and data link", 2006 IEEE International Solid-State Circuits Conference, Session 23, Technology and Architecture Directions, vol. 23.4, Feb. 8, 2006, 3 pgs.

Miura et al., "Analysis and Design of Inductive Coupling and Transceiver Circuit for Inductive Inter-Chip Wireless Superconnect", IEEE Journal of Solid-State Circuits, vol. 40, Issue 4, Apr. 2005, pp. 829-837.

Muller et al., "A Minimally Invasive 64-Channel Wireless μECoG Implant", IEEE Journal of Solid-State Circuits, Jan. 2015, vol. 50, No. 1, pp. 344-359.

Popovic et al., "Low-Power Far-Field Wireless Powering for Wireless Sensors", Proceedings of the IEEE, vol. 101, No. 6, Jun. 2013, pp. 1397-1409.

Ramrakhyani et al., "Design and Optimization of Resonance-Based Efficient Wireless Power Delivery Systems for Biomedical Implants", IEEE Transactions on Biomedical Circuits and Systems, vol. 5, No. 1, Feb. 2011, pp. 48-63.

Sample et al., "Analysis, Experimental Results, and Range Adaptation of Magnetically Coupled Resonators for Wireless Power Transfer", IEEE Transactions on Industrial Electronics, vol. 58, No. 2, Feb. 2011, pp. 544-554.

Afshar et al., "A translational platform for prototyping closed-loop neuromodulation systems", Frontiers in Neural Circuits, Jan. 22, 2013, vol. 6, Article 117, 15 pgs., https://doi.org/10.3389/fncir.2012.00117.

Alexander, "Clock recovery from random binary signals", Electronics Letters, Oct. 30, 1975, vol. 11, No. 22, pp. 541-542, DOI: 10.1049/el:19750415.

Bihr et al., "Telemetry for implantable medical devices: Part 3—Data telemetry", IEEE Solid-State Circuits Magazine, Fall 2014, vol. 6, No. 4, pp. 56-62, DOI: 10.1109/MSSC.2014.2347812.

Bohorquez et al., "A 350 μW CMOS MSK Transmitter and 400 μW OOK Super-Regenerative Receiver for Medical Implant Communications", IEEE Journal of Solid-State Circuits, Apr. 2009, vol. 44, No. 4, pp. 1248-1259, DOI: 10.1109/JSSC.2009.2014728.

Gibson et al., "Spike Sorting: The First Step in Decoding the Brain: The first step in decoding the brain", IEEE Signal Processing Magazine, Jan. 2012, vol. 29, No. 1, pp. 124-143, DOI: 10.1109/MSP.2011.941880.

Hajimiri et al., "Design issues in CMOS differential LC oscillators", IEEE Journal of Solid-State Circuits, May 1999, vol. 34, No. 5, pp. 717-724, DOI: 10.1109/4.760384.

Hu et al., "A fully integrated low-power BPSK demodulator for implantable medical devices", IEEE Transactions on Circuits and Systems I: Regular Papers, Dec. 2005, vol. 52, No. 12, pp. 2552-2562, DOI: 10.1109/TCSI.2005.858163.

Jiang et al., "An Integrated Passive Phase-Shift Keying Modulator for Biomedical Implants With Power Telemetry Over a Single Inductive Link", IEEE Transactions on Biomedical Circuits and Systems, Feb. 2017, vol. 11, No. 1, pp. 64-77, DOI: 10.1109/TBCAS.2016.2580513.

Kiani et al., "12.7 A power-management ASIC with Q-modulation capability for efficient inductive power transmission", Transactions of the IEEE International Solid-State Circuits Conference—(ISSCC) Digest of Technical Papers, San Francisco, California, Feb. 22-26, 2015, 3 pgs.

Kim et al., "Review of Near-Field Wireless Power and Communication for Biomedical Applications", IEEE Access, Sep. 27, 2017, vol. 5, p. 21264-21285, DOI: 10.1109/ACCESS.2017.2757267.

Kuan et al., "Wireless Gigabit Data Telemetry for Large-Scale Neural Recording", IEEE Journal of Biomedical and Health Informatics, May 2015, vol. 19, No. 3, pp. 949-957, DOI: 10.1109/JBHI.2015.2416202.

Lombardo et al., "16.7 A fully-integrated half-duplex data/power transfer system with up to 40Mb/s data rate, 23mW output power and on-chip 5kV galvanic isolation", 2016 IEEE International Solid-State Circuits Conference (ISSCC), Jan. 31-Feb. 4, 2016, San Francisco, CA, USA, pp. 300-301, DOI: 10.1109/ISSCC.2016.7418026.

Mirbozorgi et al., "A Single-Chip Full-Duplex High Speed Transceiver for Multi-Site Stimulating and Recording Neural Implants", IEEE Transactions on Biomedical Circuits and Systems, Jun. 2016, vol. 10, No. 3, pp. 643-653, DOI: 10.1109/TBCAS.2015.2466592.

Okun, "Deep-Brain Stimulation for Parkinson's Disease", The New England Journal of Medicine, Oct. 18, 2012, vol. 367, pp. 1529-1538, DOI: 10.1056/NEJMct1208070.

Okun, "Deep-brain stimulation—entering the era of human neural-network modulation", The New England Journal of Medicine, Oct. 9, 2014, vol. 371, pp. 1369-1373, DOI: 10.1056/NEJMp1408779.

Pan, "A General Theory of Wireless Power Transfer via Inductive Links", UCLA Electronic Theses and Dissertations, 2015, 45 pgs.

Pan et al., "22.7 An inductively-coupled wireless power-transfer system that is immune to distance and load variations", 2017 IEEE International Solid-State Circuits Conference (ISSCC), Feb. 5-9, 2017, pp. 382-383.

Shoaib et al., "A 0.6-107 μW Energy-Scalable Processor for Directly Analyzing Compressively-Sensed EEG", IEEE Transactions on Circuits and Systems I: Regular Papers, Apr. 2014, vol. 61, No. 4, pp. 1105-1118, DOI: 10.1109/TCSI.2013.2285912.

Shoaib et al., "Enabling advanced inference on sensor nodes through direct use of compressively-sensed signals", 2012 Design, Automation & Test in Europe Conference & Exhibition (Date), Mar. 12-16, 2012, Dresden, Germany, pp. 437-442, DOI: 10.1109/DATE.2012.6176511.

Tan et al., "A 2.4 GHz ULP Reconfigurable Asymmetric Transceiver for Single-Chip Wireless Neural Recording IC", IEEE Transactions on Biomedical Circuits and Systems, Aug. 2014, vol. 8, No. 4, pp. 497-509, DOI: 10.1109/TBCAS.2013.2290533.

Weaver et al., "Handbook of biological effects of electromagnetic fields", Taylor & Francis Group, LLC, 2007, Third Edition, 465 pgs.

Who, "What are neurological disorders?", May 2016, retrieved from https://web.archive.org/web/20170418102437/http://www.who.int/features/qa/55/en/ on Jul. 16, 2020.

(56) References Cited

OTHER PUBLICATIONS

Xu et al., "Design Methodology for Phase-Locked Loops Using Binary (Bang-Bang) Phase Detectors", IEEE Transactions on Circuits and Systems I: Regular Papers, Jul. 2017, vol. 64, No. 7, pp. 1637-1650, DOI: 10.1109/TCSI.2017.2679683.

Shinohara, "Beam Control Technologies With a High-Efficiency Phased Array for Microwave Power Transmission in Japan", Proceedings of the IEEE, vol. 101, No. 6, Jun. 2013, pp. 1448-1463.

Si et al., "A Frequency Control Method for Regulating Wireless Power to Implantable Devices", IEEE Transactions on Biomedical Circuits and Systems, vol. 2, No. 1, Mar. 2008, pp. 22-29.

Terman, "Radio Engineers' Handbook", McGraw-Hill Book Company, Inc., First Edition, Tenth Impression, 1943, 1036 pgs. (presented in 3 parts).

Tesla, "The True Wireless", Electrical Experimenter, May 1919, 7 pgs.

Wang et al., "Design and analysis of an adaptive transcutaneous power telemetry for biomedical implants", IEEE Transactions on Circuits and Systems I: Regular Papers, vol. 52, No. 10, Oct. 2005, pp. 2109-2117.

Yang et al., "Inductor Modeling in Wireless Links for Implantable Electronics", IEEE Transactions on Magnetics, vol. 43, No. 10, Oct. 2007, pp. 3851-3860.

Yilmaz et al., "Wireless Energy and Data Transfer for In-Vivo Epileptic Focus Localization", IEEE Sensors Journal, vol. 13, No. 11, Nov. 2013, pp. 4172-4179.

Yousefi et al., "A Distance-Immune Low-Power 4-Mbps Inductively-Coupled Bidirectional Data Link", Symposium on VLSI Circuits, Kyoto, Japan, Jun. 5-8, 2017, pp. C60-C61.

Zierhofer et al., "High-Efficiency Coupling-Insensitive Transcutaneous Power and Data Transmission Via an Inductive Link", IEEE Transactions on Biomedical Engineering, vol. 37, No. 7, Jul. 1990, pp. 716-722.

Zierhofer et al., "The class-E concept for efficient wide-band coupling-insensitive transdermal power and data transfer", Proceedings of the 14th Annual International Conference of the IEEE Engineering in Medicine and Biology Society, Paris, France, Oct. 29-Nov. 1, 1992, pp. 382-383.

\* cited by examiner

Distance Self-Regulation:
At $\omega_{L,H}$, $\text{Im}\{Y_{in}\}=0$.
$\Rightarrow$ OSC ($I_S$) operates at $\omega_{L,H}$.

Load Self-Regulation:
When $R_L \downarrow$, if $I_S$ −, $V_S \downarrow$.
$\Rightarrow$ AAC increases $I_S$
$\Rightarrow$ constant $V_S$ Because $V_S : V_2 = \sqrt{L_1} : \sqrt{L_2}$
$\Rightarrow$ constant $V_2$

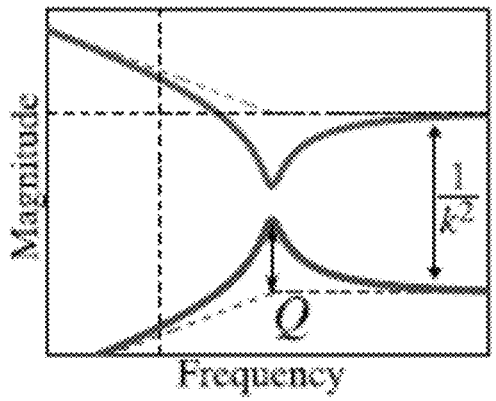
FIG. 15A  Under-coupled ($k < k_c$)
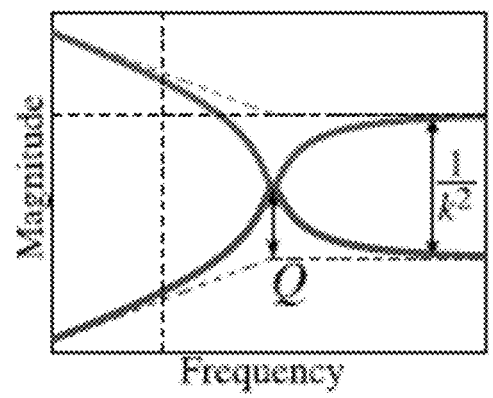
FIG. 15B  Critical coupling ($k = k_c$)
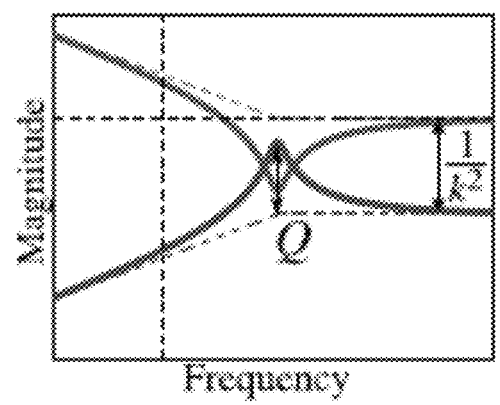
FIG. 15C  Over-coupled ($k > k_c$)

$\omega_{res,2} < \omega_{res,1}$ $\omega_{res,2} > \omega_{res,1}$

LOAD-INDUCED RESONANCE-SHIFT-KEYING MODULATION SCHEME FOR SIMULTANEOUS NEAR-FIELD WIRELESS POWER AND DATA TRANSMISSION THROUGH A PAIR OF INDUCTIVE COILS

CROSS-REFERENCE TO RELATED APPLICATIONS

The current application is a national stage of PCT Patent Application No. PCT/US2018/046779, entitled "Load-Induced Resonance-Shift-Keying Modulation Scheme for Simultaneous Near-Field Wireless Power and Data Transmission through a Pair of Inductive Coils" to Pan et al., filed Aug. 14, 2018, which claims priority under 35 U.S.C. 119(e) to U.S. Provisional Patent Application Ser. No. 62/545,303, entitled "Load-Induced Frequency-Shift-Keying: A new modulation scheme that enables simultaneous near-field wireless power and data transmission through a single set of inductive coils", filed Aug. 14, 2017 and U.S. Provisional Patent Application Ser. No. 62/558,798, entitled "Load-Induced Frequency-Shift-Keying Modulation Scheme that Enables Simultaneous Near-Field Wireless Power and Data Transmission through a Single Set of Inductive Coils", filed Sep. 14, 2017, the disclosures of which are hereby incorporated herein by reference in their entirety.

STATEMENT REGARDING FEDERALLY SPONSORED RESEARCH OR DEVELOPMENT

This invention was made with government support under Grant Number N66001-14-2-4029, awarded by the U.S. Department of Defense, Defense Advanced Research Projects Agency. The Government has certain rights in the invention.

FIELD OF THE INVENTION

The present invention generally relates to power and data links and, more specifically, simultaneous near-field wireless power and data transmission.

BACKGROUND

Implanted devices can include electronic biomedical devices used for patient monitoring, diagnostics, and various other purposes. These devices can be implanted inside a patient's body, typically by means of a surgical operation. Implanted devices can act as either sensors or stimulators. Sensors can measure biosignals, such as body temperature and blood pressure, from inside the body and transmit this information to an external device. Stimulators can receive information externally, such as from an external unit operated by medical professionals, and can produce signals within the body, such as stimulating specific nerves. Common applications of stimulators include the use of microelectrodes for diagnosing and determining treatment of brain disorders and neurological conditions. Early implanted devices were interfaced with wires through the skin in order to receive energy and transmit data. However, this arrangement can restrict the patient's movements and require bulky, rack-mounted electronics. Furthermore, because of penetration through the skin, there is a greater risk of infection. As such, a need for wireless telemetry systems exists.

SUMMARY OF THE INVENTION

One embodiment includes a wireless inductive telemetry link including an external transceiver including a demodulation circuit including a counter and a finite state machine circuit for outputting an output data signal, and an internal transceiver including a modulation circuit including a switch load capacitor for receiving an input data signal, wherein the switch capacitor is capable of receiving a data signal and modulating the data signal under a load-induced resonance-shift-keying modulation scheme, wherein the external transceiver is configured to transfer power to the internal transceiver while receiving data from the internal transceiver contemporaneously.

In another embodiment, the external transceiver further includes a first inductive coil, the internal transceiver further includes a second inductive coil, and the external is configured to transfer power to the internal transceiver while receiving data from the internal transceiver contemporaneously using the first and second inductive coils.

In a further embodiment, the load-induced resonance-shift-keying modulation scheme is implemented by using a switch capacitor to flip oscillation between two resonant frequencies, $\omega_L$ and $\omega_H$.

In still another embodiment, the demodulation circuit further includes an oscillator shut-down switch.

In a still further embodiment, the internal transceiver further includes a large capacitor for supplying charge at oscillator shut-down.

In yet another embodiment, the external transceiver is configured to provide self-regulated power to the internal transceiver.

In a yet further embodiment, the external transceiver is configured to provide self-regulated power to the internal transceiver within a coil separation $d_C$ range of 4.2 centimeters.

In another additional embodiment, the external transceiver is configured to provide self-regulated power to the internal transceiver within a coil separation $d_C$ range of 0.8 centimeters.

In a further additional embodiment, the internal transceiver is configured to transmit data to the external transceiver at a data rate of 5 Mbps.

In another embodiment again, the power transfer efficiency is above 35%.

A further embodiment again includes a method for simultaneous power and data transmission, the method including transmitting data from an internal transceiver to an external transceiver, wherein the external transceiver includes a demodulation circuit including a counter and a finite state machine circuit for outputting an output data signal, and the internal transceiver includes a modulation circuit including a switch load capacitor for receiving an input data signal, wherein the switch capacitor is capable of receiving a data signal and modulating the data signal under a load-induced resonance-shift-keying modulation scheme, and transferring power from the external transceiver to the internal transceiver contemporaneously with the transmittal of data from the internal transceiver.

In still yet another embodiment, the external transceiver further includes a first inductive coil, the internal transceiver further includes a second inductive coil, and the transmission of data and transferal of power are performed through the first and second inductive coils.

In a still yet further embodiment, the load-induced resonance-shift-keying modulation scheme is implemented by using a switch capacitor to flip oscillation between two resonant frequencies, $\omega_L$ and $\omega_H$.

In still another additional embodiment, the demodulation circuit further includes an oscillator shut-down switch.

In a still further additional embodiment, the internal transceiver further includes a large capacitor for supplying charge at oscillator shut-down.

In still another embodiment again, the external transceiver is configured to provide self-regulated power to the internal transceiver.

In a still further embodiment again, the external transceiver is configured to provide self-regulated power to the internal transceiver within a coil separation $d_C$ range of 4.2 centimeters.

In yet another additional embodiment, the external transceiver is configured to provide self-regulated power to the internal transceiver within a coil separation $d_C$ range of 0.8 centimeters.

In a yet further additional embodiment, the data is transmitted to the external transceiver at a data rate of 5 Mbps.

In yet another embodiment again, the power is transferred with a power transfer efficiency above 35%.

Additional embodiments and features are set forth in part in the description that follows, and in part will become apparent to those skilled in the art upon examination of the specification or may be learned by the practice of the invention. A further understanding of the nature and advantages of the present invention may be realized by reference to the remaining portions of the specification and the drawings, which forms a part of this disclosure.

BRIEF DESCRIPTION OF THE DRAWINGS

The description will be more fully understood with reference to the following figures, data graphs, and diagrams, which are presented as exemplary embodiments of the invention and should not be construed as a complete recitation of the scope of the invention.

FIGS. 15A-15C show graphical representations of three power transfer scenarios with respect to the coupling coefficient k in accordance with various embodiments of the invention.

DETAILED DESCRIPTION

Biomedical implants in accordance with various embodiments of the invention can be implemented in many different ways. In many embodiments, the implants are configured to receive power and transmit data wirelessly. In further embodiments, the implants are configured to simultaneously receive power and transmit data. Such devices can be configured to receive power from an external source and transmit data, such as but not limited to recorded neural data and/or other biological data, to outside the body. In many cases, the data is transmitted to the device that delivers power to the implant. For example, the power and data transmission system can be implemented with a pair of transceivers. The implant transceiver can receive power wirelessly though an external transceiver while simultaneously transmitting data to the external transceiver. In several embodiments, both forward (power) and reverse (data) links use the same pair of inductive coils in the transceivers, one coil mounted in the implant and the other in the external unit. The forward power link can be configured to deliver tens of mW to drive multiple stimulator engines. The reverse data link can be configured to support rates as high as a few Mb/s to transmit multiplexed neural waveforms sensed from an array of electrodes. In some embodiments, the system is configured to deliver self-regulated power to the implant. In several embodiments, the devices are configured for simultaneous power and data transmissions at reasonable distances. The delivered voltage at the implant can be regulated over changes in coil distance, misalignment, and/or load current. In a number of embodiments, the voltage remain constant as the distance between the coils changes or if their axes misalign. In further embodiments, the system is designed such that when data is transmitted over the power-carrying waveform, it does not induce a noticeable ripple on the rectified voltage supplying the implant current. Wireless data and power transmission systems are discussed below in further detail.

Data Modulation

Figure 1:
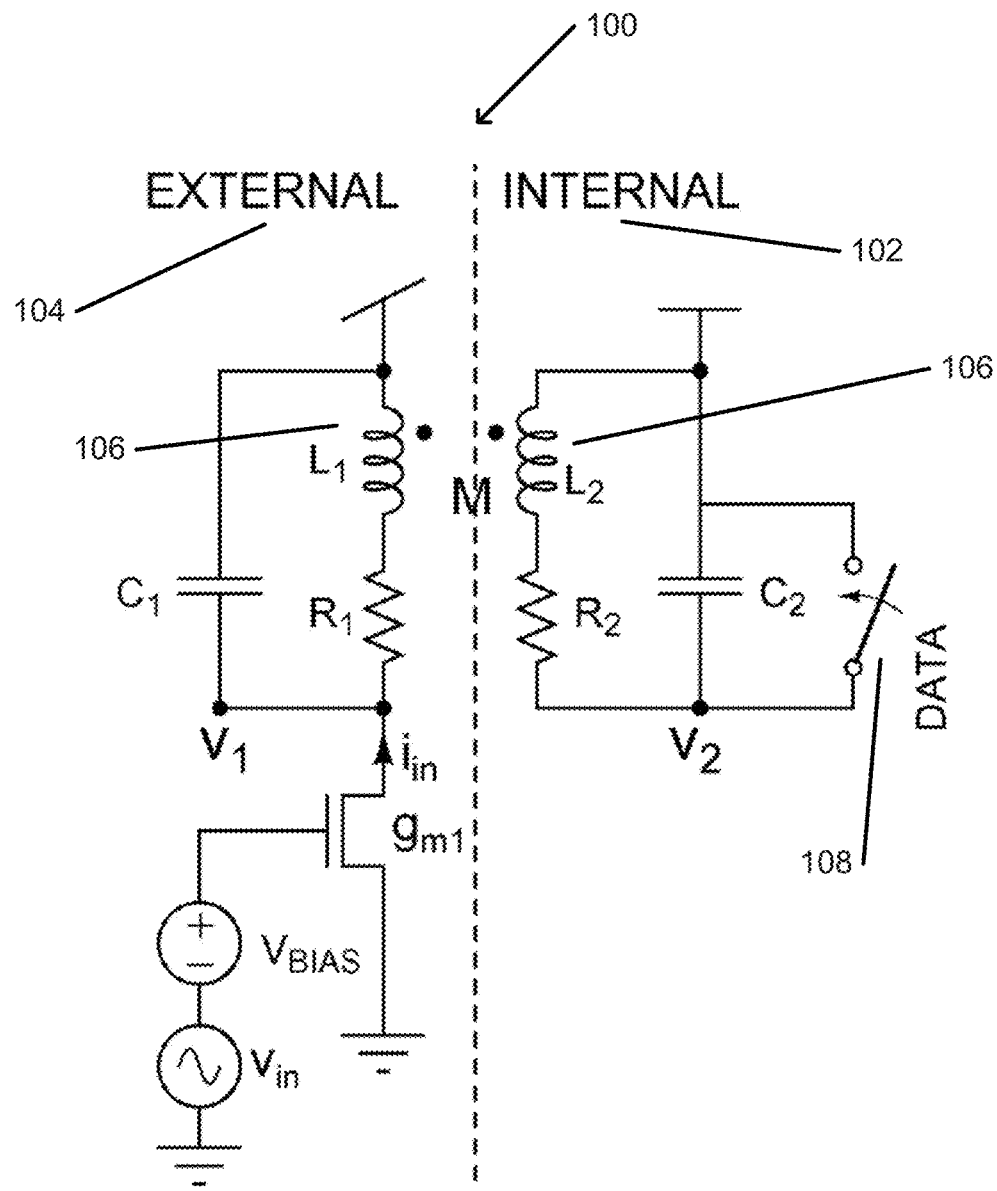
FIG. 1 conceptually illustrates a circuit diagram of an external transceiver and an internal transceiver utilizing a load shift keying system for carrier signal modulation.

Many different methods of transmitting data through wireless inductive telemetry links can be implemented, such as but not limited to carrier based modulation. Carrier based modulation is a scheme that can be used to transmit data by varying a periodic waveform, called the carrier signal. Modulation schemes can include but are not limited to load modulation, amplitude modulation, frequency modulation, and/or phase modulation. The modulated signal can be demodulated in the receiving device to retrieve the source waveform. Different modulation schemes can have different advantages and utilities. Important considerations in determining which modulation scheme to utilize can include the amount of power consumption and the ability to transmit power and data simultaneously. For example, load shift keying can transmit data at low power, but it can be difficult to transmit power and data simultaneously. A circuit diagram of an external transceiver and an internal transceiver utilizing a load shift keying system for carrier signal modulation is conceptually illustrated in FIG. 1. As shown, the system 100 includes an internal transceiver 102 sending data to an external transceiver 104 using a pair of inductor coils 106 and a data switch 108 for modulation.

Figure 2:
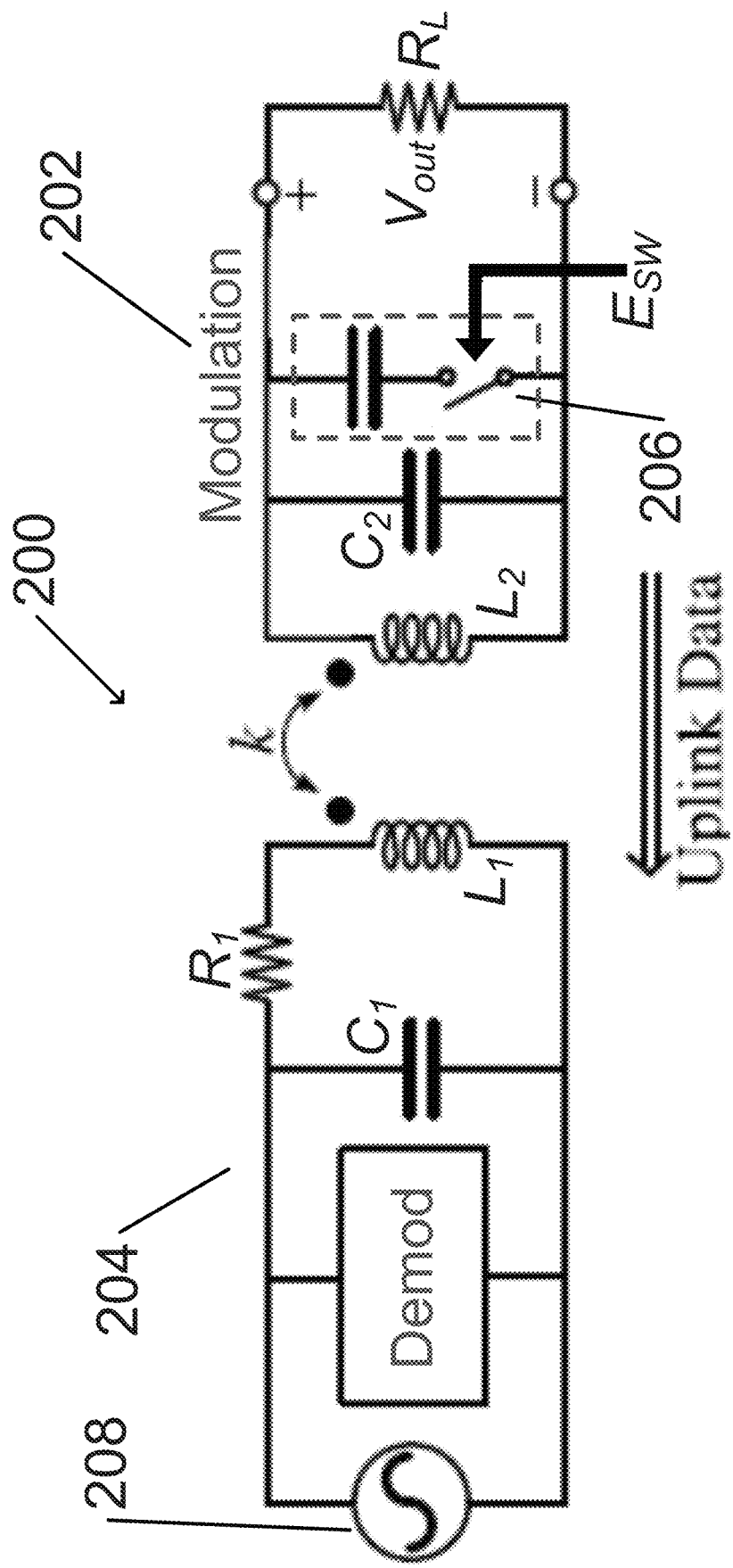
FIG. 2 conceptually illustrates a diagram detailing the architecture of a telemetry link system utilizing load-induced resonance-shift-keying modulation in accordance with an embodiment of the invention.

Data transmission systems in accordance with various embodiments of the invention can be implemented using a low-power, high-rate modulation scheme. In some embodiments, a load-induced resonance-shift-keying ("L-RSK") modulation scheme is used to transmit data between transceivers. L-RSK can be used as a low-powered, high rate data transmission scheme and can be implemented through the switching of a load capacitor to modulate an input signal, or carrier signal. A diagram detailing the architecture of a telemetry link system utilizing L-RSK in accordance with an embodiment of the invention is conceptually illustrated in FIG. 2. The telemetry link system 200 can include an implanted transceiver 202 and an external transceiver 204. The implanted transceiver 202 can be used to transmit data, termed uplink data, to an external transceiver 204 while simultaneously receiving power. As shown in the exemplary embodiment, the implanted transceiver 202 implements a switch capacitor 206 that can be used to induce a load. This load induced modulation scheme typically consumes low power. In various embodiments, the external transceiver 204 can include an oscillator driver component 208. The oscillator side can be configured to maintain a constant envelope, which can facilitate consistent and uninterrupted power transmission. In several embodiments, the modulated signal can be demodulated by sensing the frequency.

Figure 3:
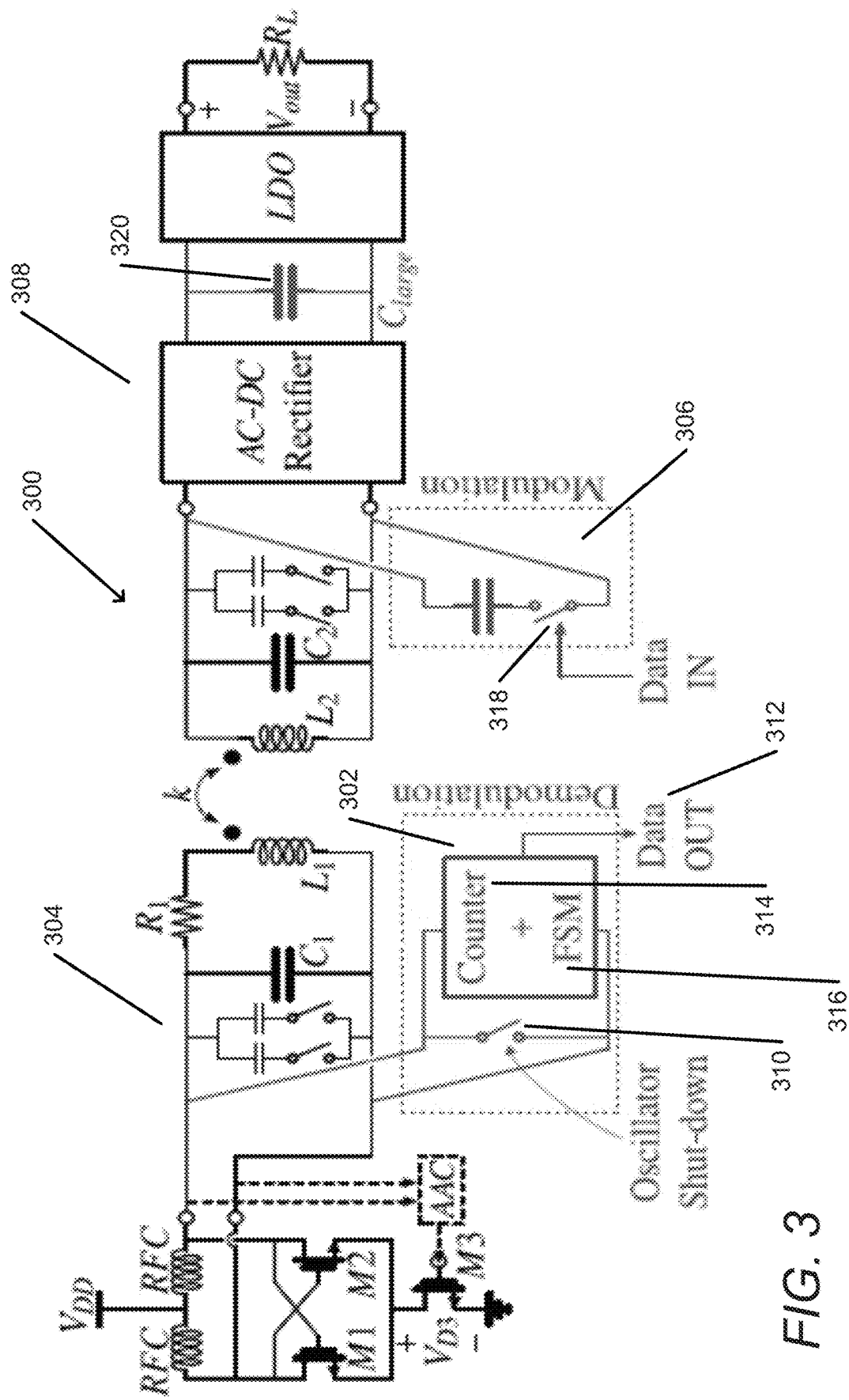
FIG. 3 conceptually illustrates a detailed circuit diagram of a telemetry link system in accordance with an embodiment of the invention.

FIG. 3 conceptually illustrates a detailed circuit diagram of a telemetry link system in accordance with an embodiment of the invention. As shown, the data transmission circuitry 300 can include a demodulation circuit 302 implemented in an external transceiver 304 and a modulation circuit 306 implemented in an implanted transceiver 308. The demodulation circuit 302 can include an oscillator shut-down switch 310 and a circuit for outputting data 312. In various embodiments, the data output circuit 312 can include a counter 314 and a sequential circuit implementing a finite state machine ("FSM") 316. The modulation circuit 306 can include a switch capacitor 318 that can implement L-RSK by modulating a source waveform in accordance with a data input. In many embodiments, switching activity can occur within an oscillator shut-down window. In several embodiments utilizing L-RSK, when the oscillator starts up, the received signal can be demodulated by measuring the frequency. In the illustrative embodiment, the implanted transceiver 308 includes a large capacitor 320 at rectifier load, which can supply charge at oscillator shut-down.

Although specific modulation schemes are described above, a person having ordinary skill in the art would appreciate that other modulation schemes can be used in accordance with the requirements of a given application. For example, in some embodiments, an amplitude shift keying ("ASK") scheme is used to modulate a carrier signal. Different modulation schemes can have varying degrees of performance with respect to power consumption, noise performance, data transmission rate, and other performance metrics. For instance, frequency shift keying ("FSK") can have better noise performance than ASK for some applications.

Wireless Power Transfer System

Near-field wireless power transfer systems can be implemented in a variety of different ways, such as but not limited to the use of inductive links. An inductive link-based wireless power transfer system generally includes a power transmitter, where power originates, followed by a power transfer link through which power could flow from source to load. A power receiver can harvest power from the link and deliver it to the load. In many embodiments, an inductive link-based wireless power transfer system can be implemented using coupled inductor coils with which power carrying electromagnetic waves are linked. The power transfer distance can be comparable to the physical dimensions of the inductor coils and can achieve a high power transfer efficiency. Power transmitters can be considered as energy sources and can be equivalently treated as voltage sources, current sources, or combinations of both. These energy sources can be implemented in a variety of ways. For example, an LC oscillator, which can be considered as a current source, can be implemented as a cross-coupled field-effect transistor ("FET") pair followed by an LC-tank circuit. The oscillator driver can be followed by a resonator link, delivering power to a resistive load.

Figure 4:
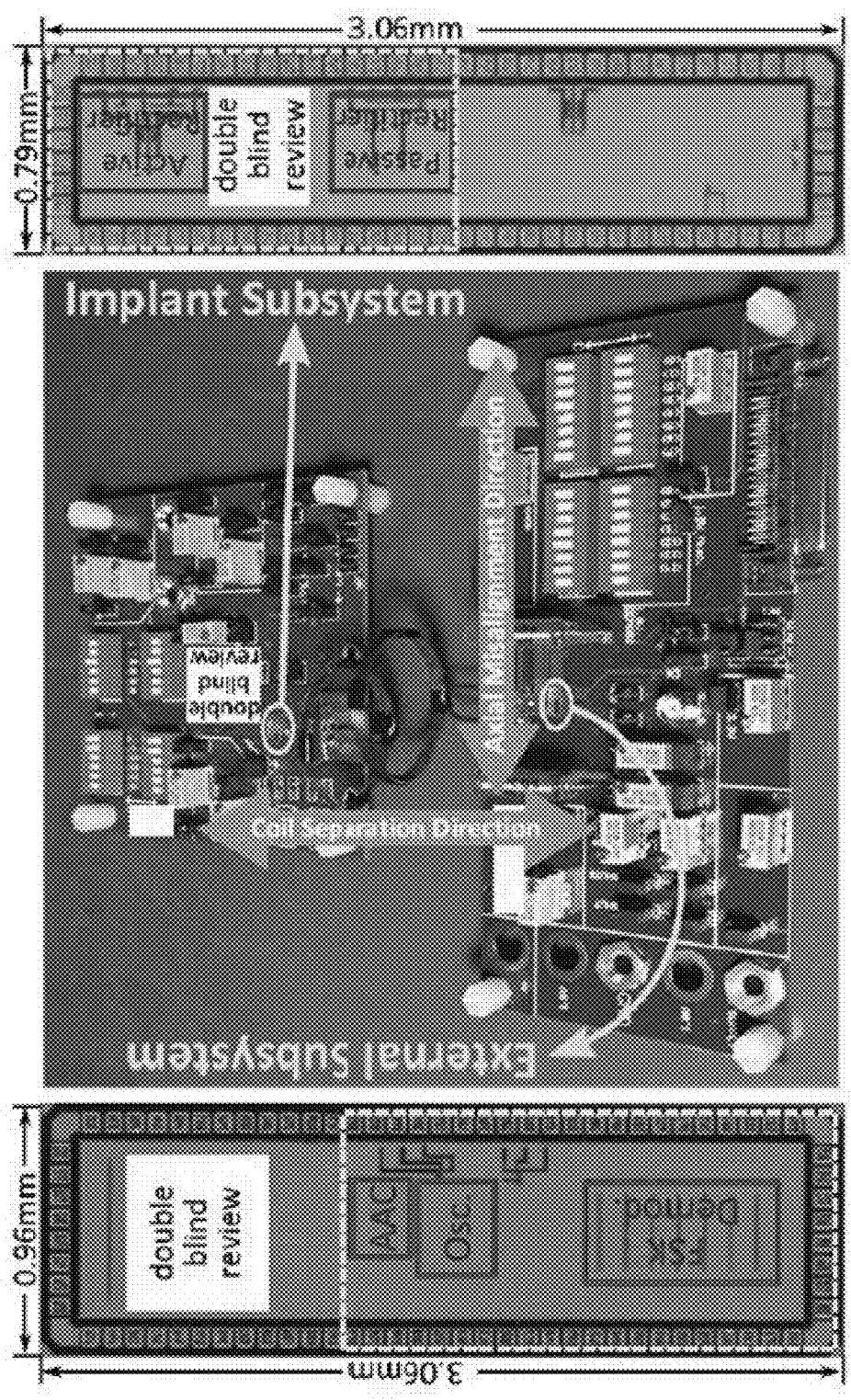
FIG. 4 shows a photograph of a test setup and micrographs of chips in accordance with an embodiment of the invention.

FIG. 4 shows a photograph of a test setup and micrographs of chips in accordance with an embodiment of the invention. As shown, coil separation and axial misalignment of the external and internal subsystems can be studied with such a test setup. There is a trade-off between delivered power $P_L$ and maximum regulation distance $d_C$:

$$|V_2|^2/(2R_L) = \boxed{P_L \uparrow} \Leftarrow \boxed{R_L \downarrow} \Rightarrow k_C = 1/Q_2 \approx (\omega_{res} L_2)/$$
$$R_L \uparrow \Rightarrow \boxed{d_C \downarrow}.$$

The resonant frequency can be configured to expand the range of regulation distance and load variations.

Figure 5:
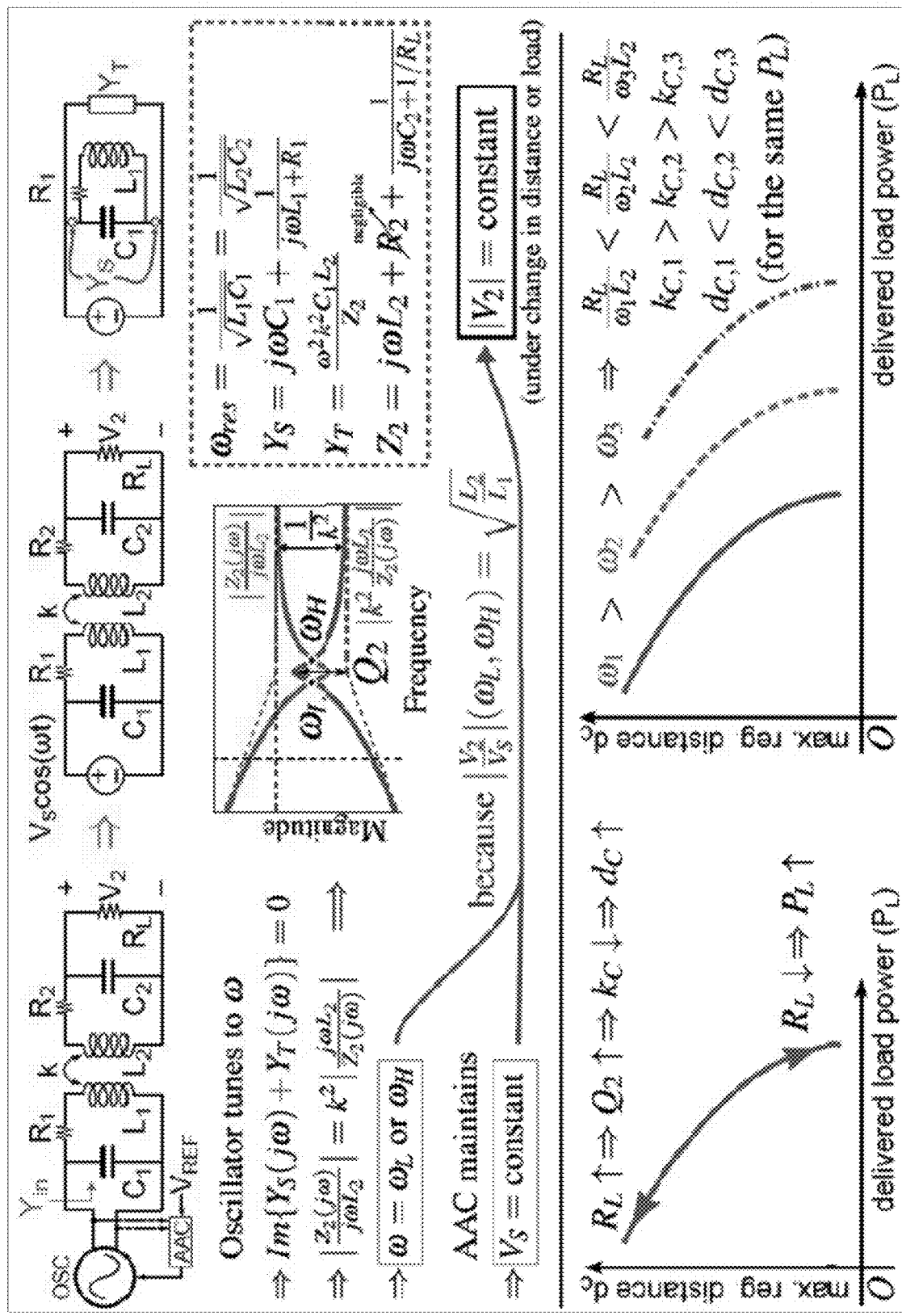
FIG. 5 conceptually illustrates the principle operation of a free-running oscillator with automatic amplitude control as the driver of a wireless power system in accordance with an embodiment of the invention.

FIG. 5 conceptually illustrates the principle operation of a free-running oscillator with automatic amplitude control ("AAC") as the driver of a wireless power system in accordance with an embodiment of the invention. In the illustrative embodiment, the free-running oscillator with AAC can appear in steady-state to the admittance ($Y_{in} = Y_S + Y_T$) as a constant-amplitude voltage source ($Y_S$) of variable frequency (around $\omega_{res}$). The oscillator can self-tune to one of a pair of frequencies such that the coupled inductors act as a transformer of fixed turns ratio ($\sqrt{(L_1/L_2)}$) over a range of coupling coefficients $k_C < k < 1$. Within this range, a constant $V_S$ maintained by AAC implies that the voltage amplitude $V_2$ on the secondary is also constant even as the implant load $R_L$ changes. Regulation can be maintained up to a maximum coil separation ($d_C$) or axial misalignment, where the coupling coefficient drops below the critical value ($k_C = 1/Q_2$).

Figure 6:
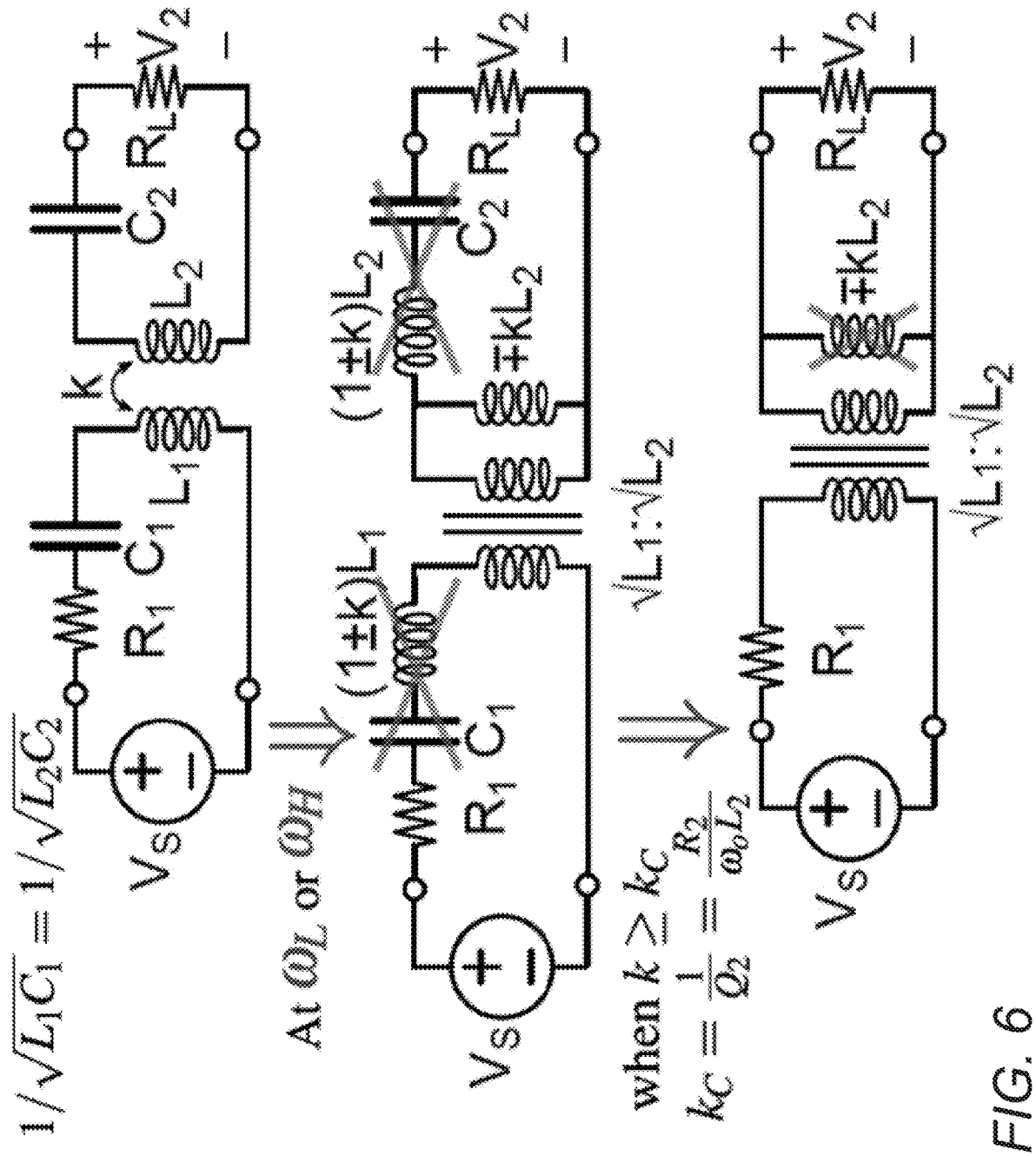
FIG. 6 conceptually illustrates the principle operation of self-regulated power over changes in distance and in load in accordance with an embodiment of the invention.
Figure 7:
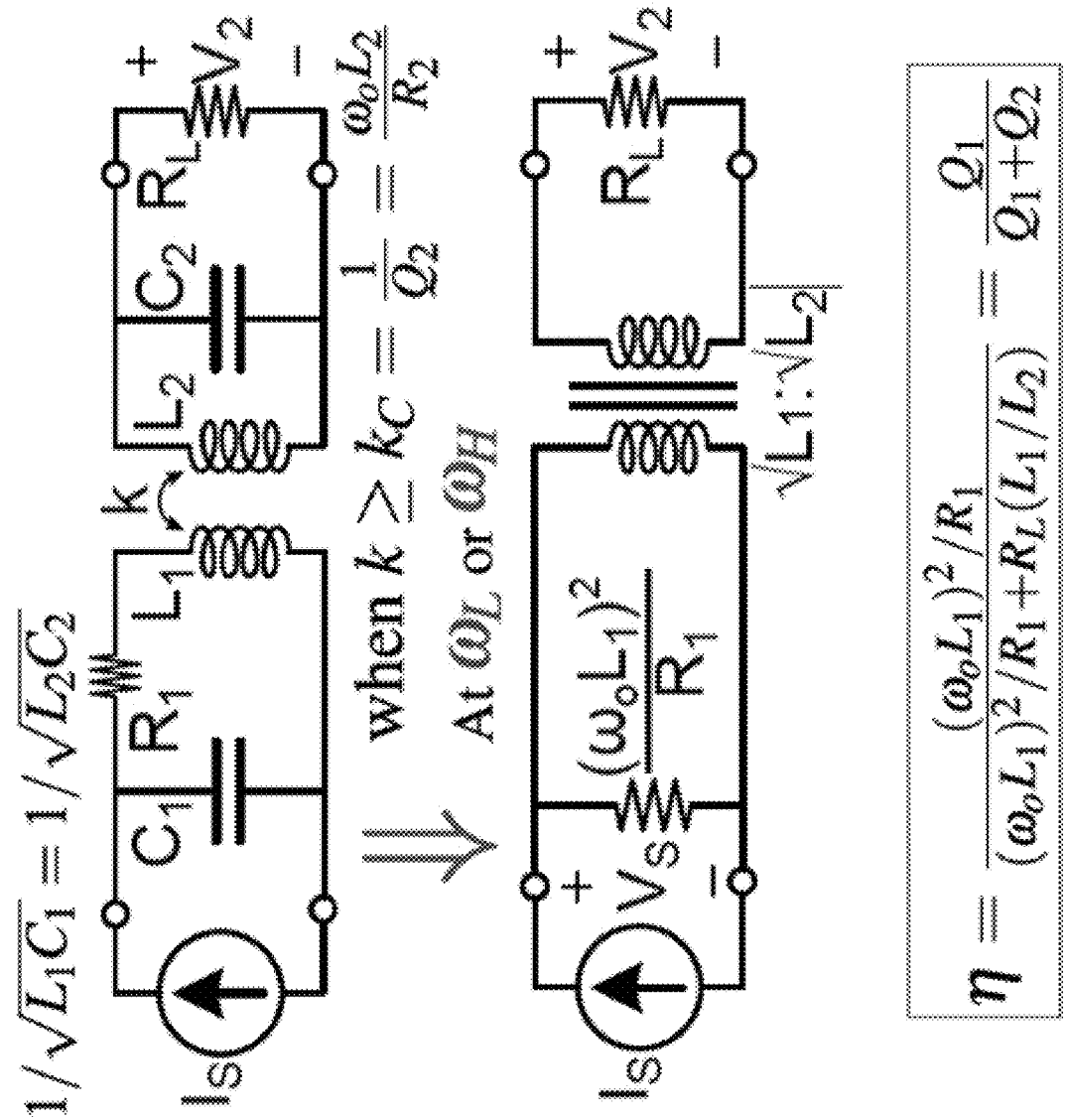
FIG. 7 conceptually illustrates an exemplary circuit with parallel resonators in accordance with an embodiment of the invention.

FIG. 6 conceptually illustrates the principle operation of self-regulated power over changes in distance and in load in accordance with an embodiment of the invention. As shown, coupled inductors are modeled by a T-network of inductors that depend on ±k, with an ideal transformer of turns ratio $\sqrt{(L_1/L_2)}:1$ in between. The "±" accounts for the in-phase (common) and anti-phase (differential) modes of operation. Provided that each resonator, when uncoupled, is tuned to the same $\omega_0 = 1/\sqrt{L_1/C_1} = 1\sqrt{L_2/C_2}$, then when coupled with coefficient k, inductors in the primary and secondary sides will both resonate with their series capacitors at one of two new natural mode frequencies, $\omega_{L,H} = \omega_0/\sqrt{1 \pm k}$. If $k\omega_0 L_2 \gg R_L$, the driving voltage source is loaded by $R_1$ and a transformed resistance $(L_1/L_2)R_L$ that is independent of k⇒the actual $R_L$ receives a constant power. This can be considered distance self-regulation. As $k\omega_0 L_2 \rightarrow R_L$, this will no longer hold, setting a lower limit on k where self-regulation ceases: $k_C = R_L/\omega_0 L_2 = 1/Q_2$. The higher the loaded $Q_2$, the larger the range of distance self-regulation ($d_C$). Although coupled series resonators are discussed, the same properties can hold for coupled parallel resonators, but now $k_C = \omega_0 L_2/R_L$. FIG. 7 conceptually illustrates an exemplary circuit with parallel resonators in accordance with an embodiment of the invention.

Figure 8A:
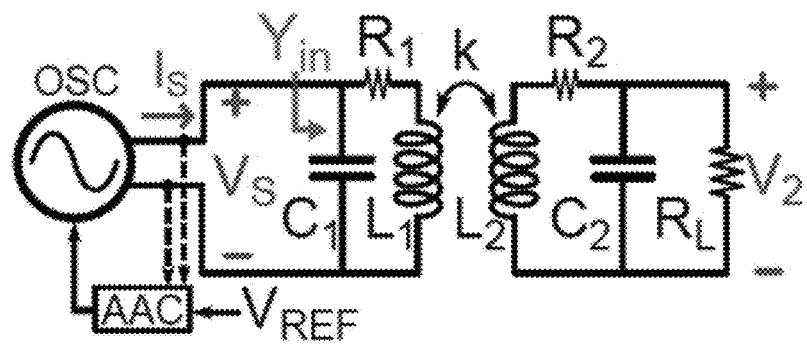
FIG. 8A conceptually illustrates an oscillator with automatic amplitude control capable of distance and load self-regulation in accordance with an embodiment of the invention.
Figure 8B:
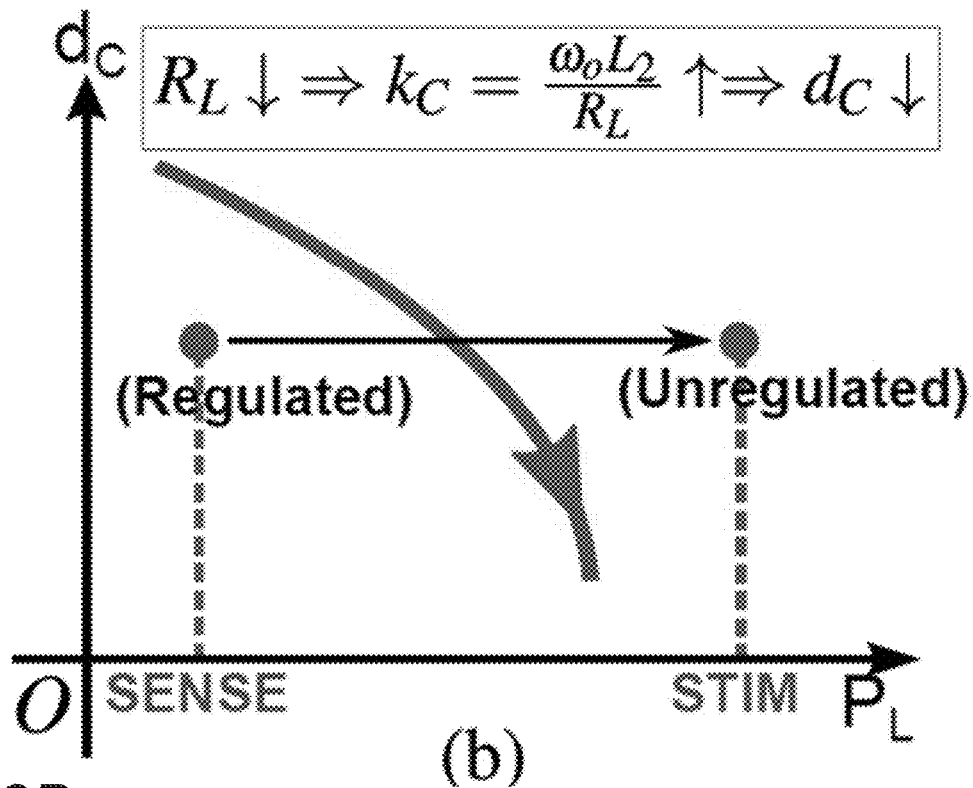
FIG. 8B shows a graph depicting how a smaller load can reduce the regulation range in accordance with an embodiment of the invention.
Figure 8C:
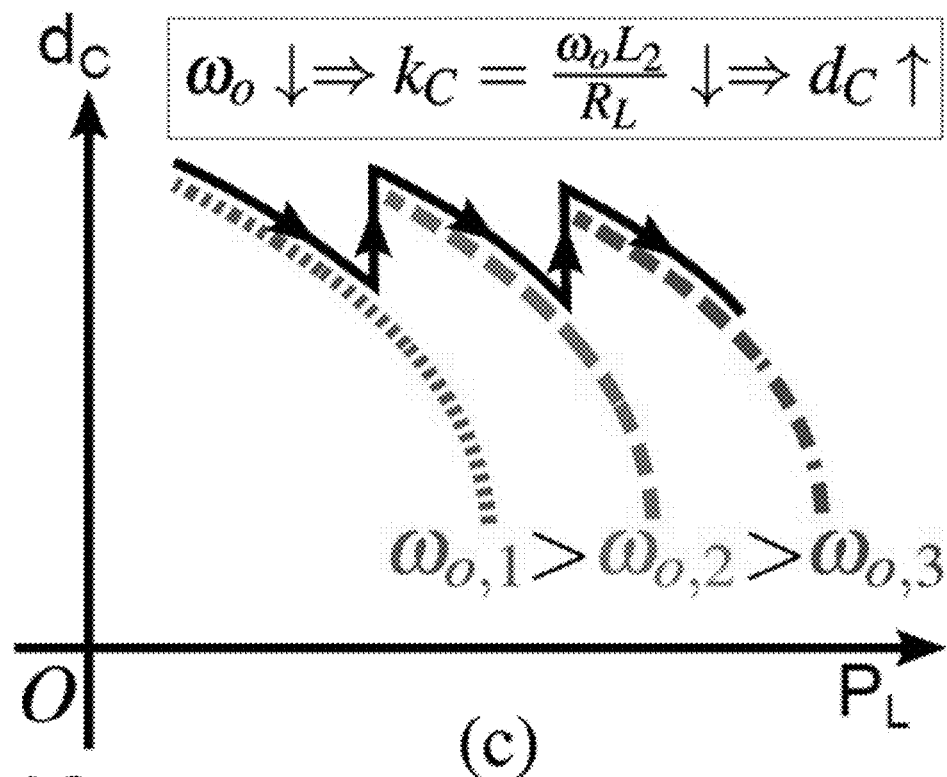
FIG. 8C shows a graph depicting load-range expansion by reducing $\omega_0$ when out-range happens in accordance with an embodiment of the invention.

FIG. 8A conceptually illustrates an oscillator with AAC capable of distance and load self-regulation in accordance with an embodiment of the invention. The current-mode oscillator tuned by the coupled resonators can operate at one natural mode, i.e. tracks one of $\omega_{L,H}$ as distance changes for $k > k_C$ so that power delivery remains distance-regulated. When the implant is stimulated with a large current, the effective $R_L$ can drop, causing oscillation amplitude to also drop. An AAC compares it with a DC reference and adjusts the commutated bias current $I_S$ to restore the amplitude. This maintains a constant $V_2$ at the implant as load varies. This can be considered load self-regulation. However, the smaller $R_L$ can raise $k_C$, which could put the coils at their present separation outside the range of distance self-regulation. FIG. 8B shows a graph depicting how a smaller load can reduce the regulation range in accordance with an embodiment of the invention. This condition can be detected by sensing over-range in the digital-to-analog converter of the AAC. The rise in $k_C$ can be counteracted by lowering $\omega_0$ (FIG. 8C) with switched capacitor banks. Conversely, when the implant is in sensing mode, $R_L \uparrow$. $\omega_0$ can then be tuned higher for better efficiency (FIG. 7: $\omega_0 \uparrow \Rightarrow \eta \uparrow$), supporting a higher data rate.

Figure 9A:
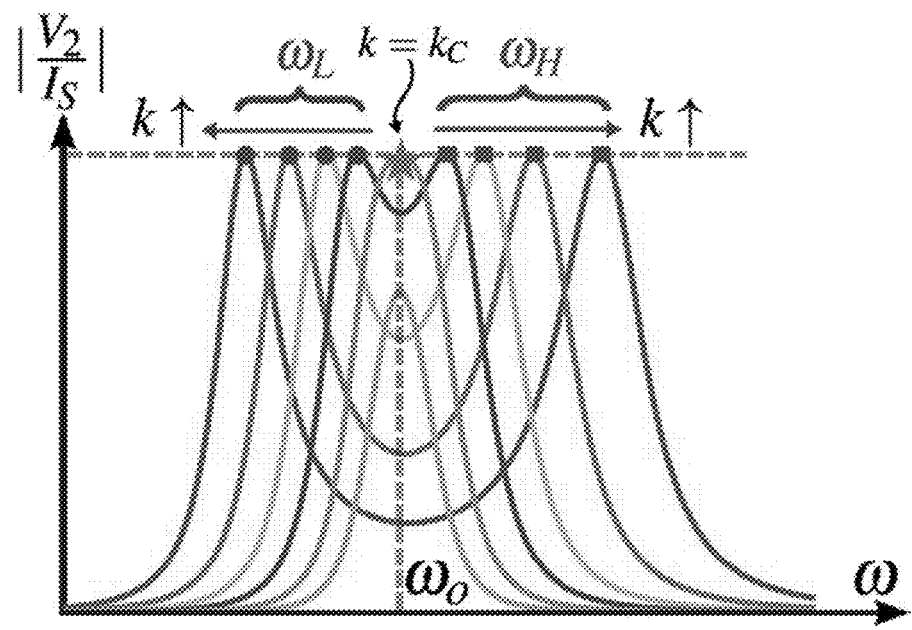
FIGS. 9A-9C show graphs depicting the splitting of $\omega_{L,H}$ for $k > k_C$ for self-regulating power in accordance with various embodiments of the invention.
Figure 9B:
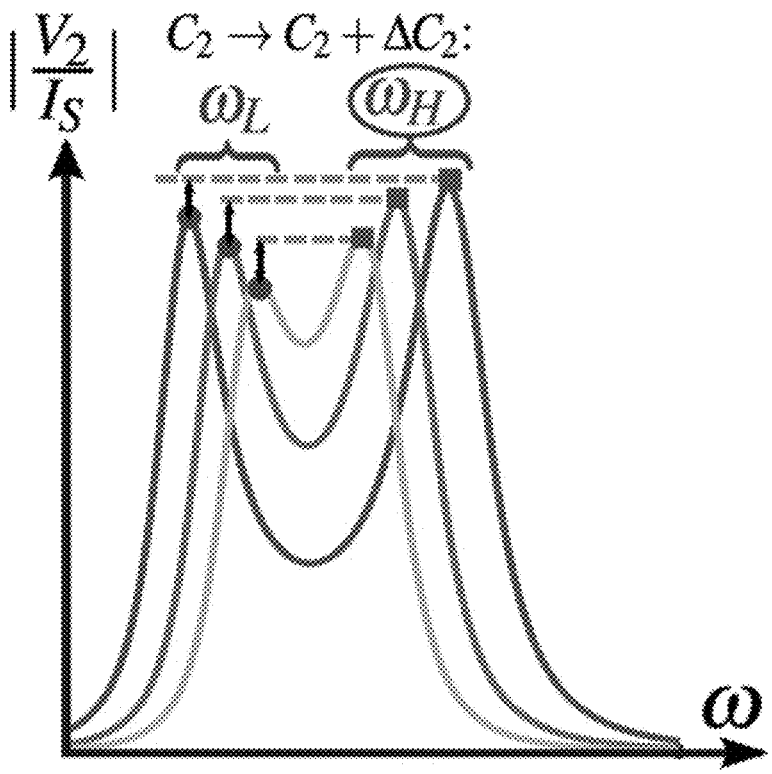
Figure 9C:
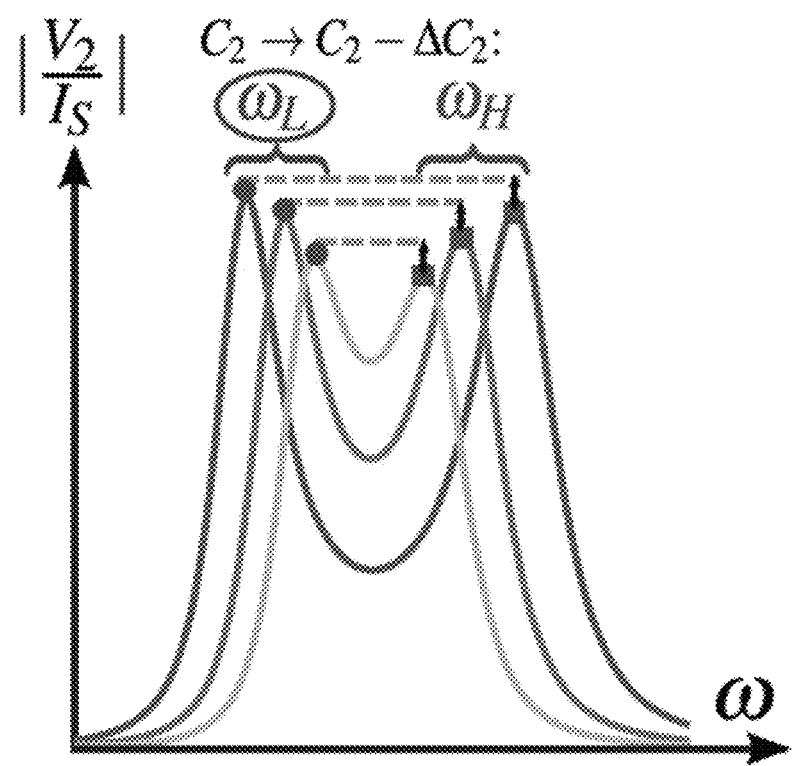
Figure 10:
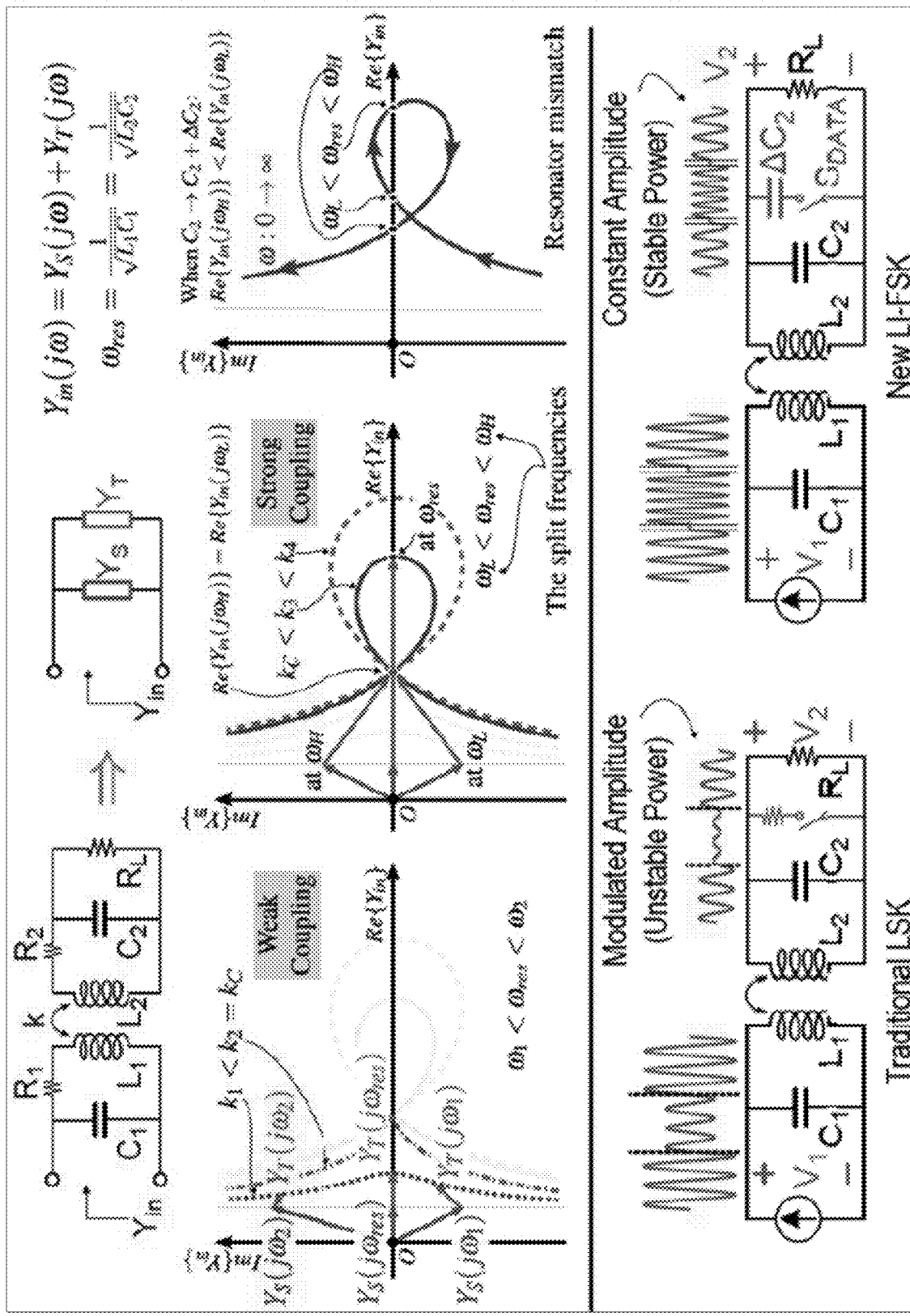
FIG. 10 shows the input admittance $Y_{in}(j\omega)$ of coupled resonators in the complex plane with frequency as a parameter in accordance with an embodiment of the invention.

Many embodiments of the invention include methods of modulation for sending data from the implant to the external unit without inducing ripple on the delivered voltage. In some embodiments, the oscillator will choose one of the two modes $\omega_{km}$. FIGS. 9A-9C show graphs depicting the splitting of $\omega_{L,H}$ for $k > k_C$ for self-regulating power in accordance with various embodiments of the invention. FIG. 10 shows the input admittance $Y_{in}(j\omega)$ of coupled resonators in the complex plane with frequency as a parameter in accordance with an embodiment of the invention. Oscillation can occur at a frequency where $\angle Y_{in} = 0$, as set by the Barkhausen stability criterion. When the resonators are weakly coupled ($0 \leq k \leq k_C$), $\angle Y_{in} = 0$ at resonant frequency $\omega_{res}$. For stronger coupling ($k_C \leq k \leq 1$), $\angle Y_{in} = 0$ at three frequencies: the resonant frequency and two bifurcated frequencies, $\omega_L \leq \omega_{res} \leq \omega_H$, which split apart as k rises. Oscillation is possible, in principle, at any of the three frequencies, but can be unstable at $\omega_{res}$ as perturbations can drive it away to settle stably into one of the two split frequencies. As shown in FIG. 10, if the oscillator's tuning admittance is smaller at $\omega_H$, then at startup the oscillation mode at $\omega_H$ sees a higher loop gain and therefore grows faster in amplitude and forces the nonlinearity in the active circuit to suppress the mode at $\omega_L$. In this instance, the mode at $\omega_H$ can prevail in steady state. This asymmetry in admittance can be deliberately induced by off-tuning the two resonators after adding or removing a small $\Delta C_2$. Thus, oscillation can be repeatably initiated at either $\omega_L$ or $\omega_H$.

Ideally, while data is being continuously uplinked, downlinked power should be delivered without noticeable ripple. The most common data modulation used in inductive links (LSK) typically fails to meet this criterion. In order to be detected, it must modulate the amplitude of $V_2$ substantially, thus inducing ripples on the load supply voltage. For smooth delivery of power, a constant envelope modulation such as FSK will be preferred. Switching $\Delta C_2$ in the implant will toggle oscillation frequency. However, for smooth power flow, $\Delta C_2$ should be $\ll C_2$, thus making it difficult to detect the resulting narrowband FSK when the data rate (~1 Mb/s) is as high as 10% of the carrier frequency (~13 MHz). However, uniquely to this system (L-RSK), the same $\Delta C_2$ can induce a shift in frequency that is almost ten times larger by forcing the oscillation to jump between the two modes—i.e., $\omega_L$ to $\omega_H$ or vice-versa. At every non-return-to-zero ("NRZ") data transition, the oscillation can be quenched (shut down), the switch $S_{DATA}$ toggled, and the oscillation restarted to acquire the other mode. Unlike LSK where the amplitude of $V_2$ is modulated over entire bit periods, oscillation quench and restart in L-RSK take place over transition edges. The bit rate can be independent of carrier frequency, and L-RSK needs only a simple non-coherent demodulator.

L-RSK modulation schemes can modulate data by switching a tiny $\Delta C_2$ (≈0.05 $C_2$) to flip oscillation between resonant modes $\omega_L$ and $\omega_m$ two frequencies whose ratio is $\sqrt{(1+k)/(1-k)}$. For $k_C < k < 1$, this ratio is large so that the frequency difference can be easily detected. At either mode frequency, the properties of self-regulation are preserved. The modulator typically consumes only the power to toggle a switch, similar to the commonly used LSK; but now the oscillation maintains an almost constant envelope for stable power flow. L-RSK is in effect a wideband binary FSK that ensures power is being transferred at $\omega_{L,H}$. If the FSK were realized by switching a large $\Delta C_2$ at implant side, then it could strongly mistune the two resonators, sacrificing power self-regulation. L-RSK can maintain self-regulated wireless power delivery while communicating data in the reverse link at a high rate.

Figure 11:
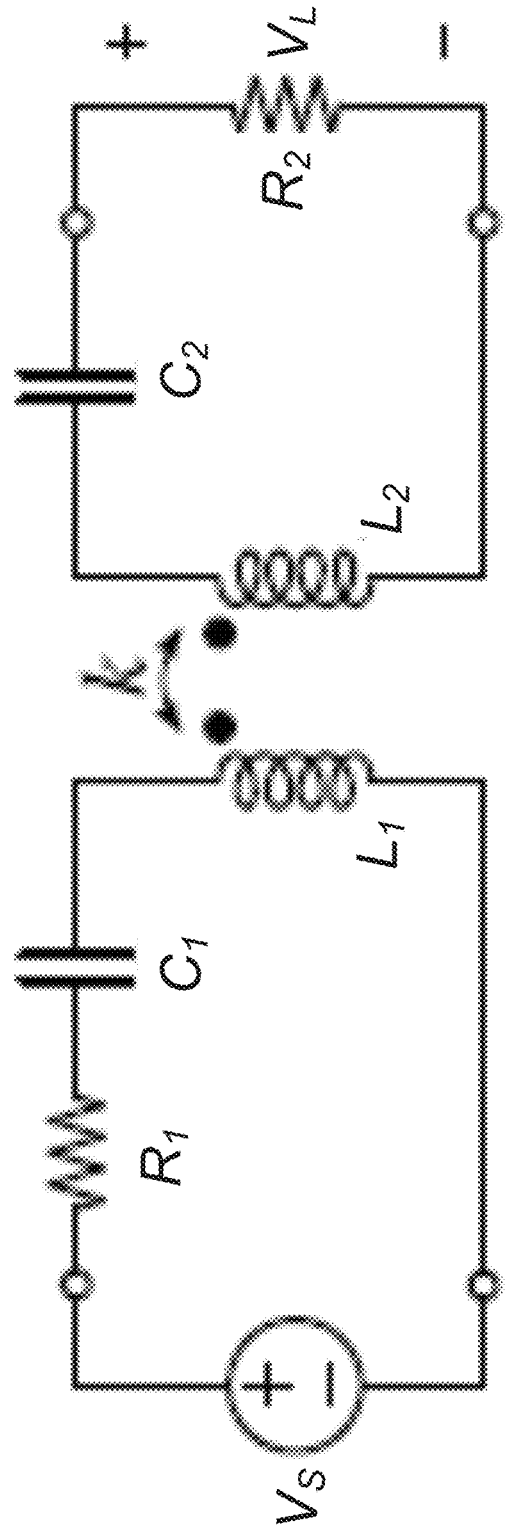
FIG. 11 conceptually illustrates a series-LCR circuit implementing a power link in accordance with an embodiment of the invention.

Different types of circuitry can be implemented to realize an inductive link. In some embodiments, a parallel-LCR power link is used as the inductive link. In other embodiments, a series-LCR power link is used as the inductive link. Choice of power link used can be considered based on various factors, such as but not limited to the type of source transmitter. For example, a parallel-LCR power link can preferably be considered if the power source transmitter is a current source power transmitter. For a voltage source power transmitter, a series-LCR power link can be the preferred implementation. A series-LCR circuit implementing a power link in accordance with an embodiment of the invention is conceptually illustrated in FIG. 11. In the illustrated embodiment, the power transmitter is modeled as a voltage source $V_S$ while the power receiver is modeled as a constant resistor $R_2$.

Although the discussions above describe specific implementations of inductive power link systems, a person having ordinary skill in the art would understand that a variety of circuit designs exists and can be implemented. For example, equivalent circuits can be exchanged as appropriate to produce the same or a similar effect.

Figure 12:
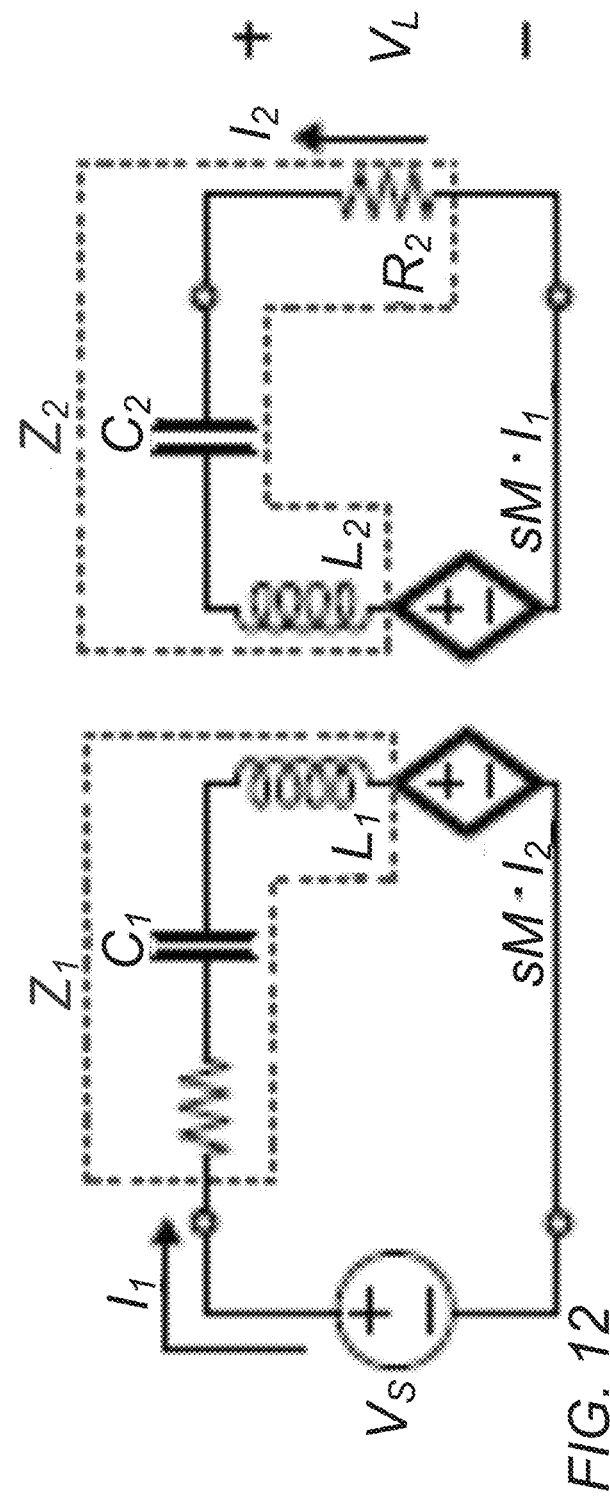
FIG. 12 conceptually illustrates a series-LCR power link with which a circuit analysis can be performed in accordance with an embodiment of the invention.

Circuit analysis can be performed on wireless power links to provide design intuition that can influence performance of the circuit. FIG. 12 conceptually illustrates a series-LCR power link with which a circuit analysis can be performed in accordance with an embodiment of the invention. As shown, an equivalent circuit can be used to replace the inductor coupling with controlled energy sources. In the illustrated embodiment, feedback analysis shows the transfer function as:

$$H(s) = \frac{V_L(s)}{V_S(s)} = -\frac{R_2}{sM} \cdot \frac{T(s)}{1+T(s)}, T(s) = \frac{-(sM)^2}{Z_1(s) \cdot Z_2(s)},$$

where $Z_1(s)=1/sC_1+R_1+sL_1$ and $Z_2(s)=1/sC_2+R_2+sL_2$ are the series impedances.

The system's input impedance under feedback can be calculated as:

$$=Z_{in,fb}=Z_{in}|_{T\to 0} \cdot (1+T)$$

$$\Rightarrow Z_{in}=Z_1 \cdot (1+T)=Z_1+Z_r.$$

Figure 13A:
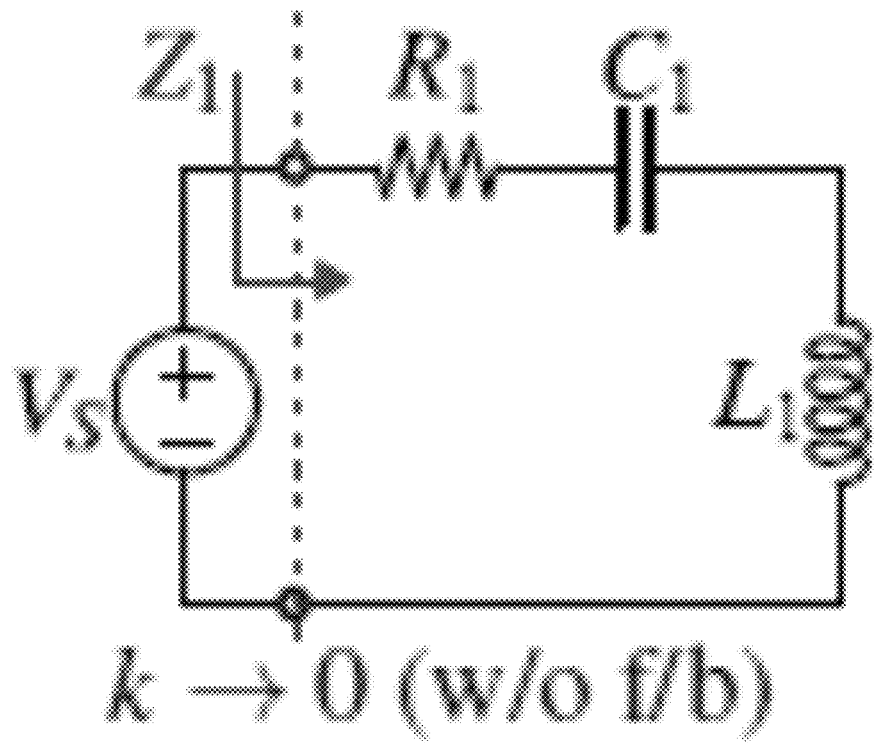
FIGS. 13A and 13B conceptually illustrate input impedance in a series-LCR circuit under feedback.
Figure 13B:
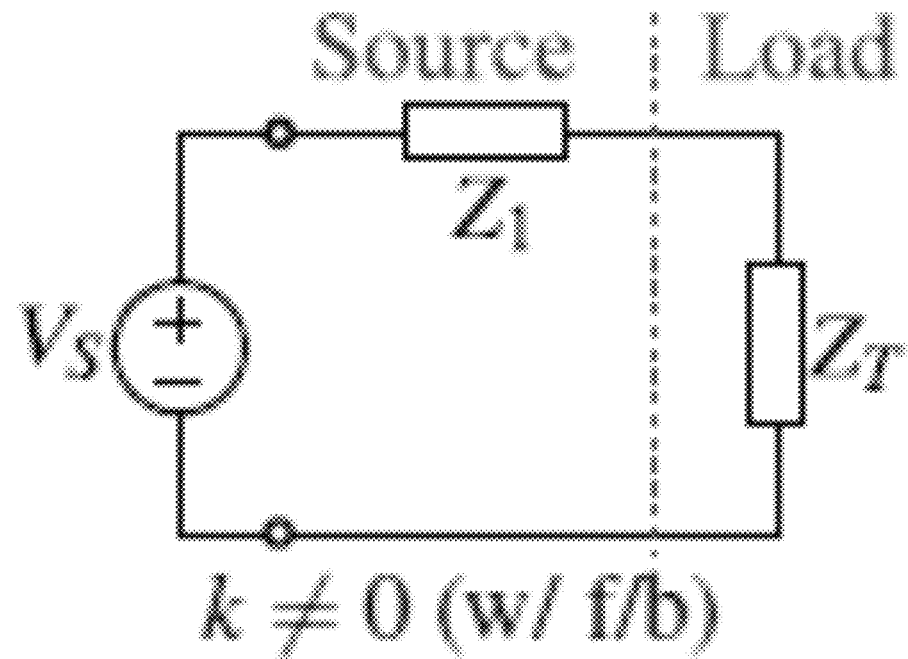

Equivalently, the circuit can be drawn as a source $V_S$ driving an impedance $Z_1$ in series with a transformed impedance $Z_T$ that is dependent on the rest of the circuit. A series-LCR system with input impedance is conceptually illustrated in FIG. 13A, and the transformed impedance for the series-LCR system is conceptually illustrated in FIG. 13B. In FIG. 13B, $Z_1$ can be considered the original $L_1$, $C_1$, and $R_1$ associated with the transmitter-side network.

$$Z_T = Z_1 \cdot T = \frac{-s^2 k^2 L_1 L_2}{Z_2}$$

is effectively the impedance looking at the port over the left controlled source $sM \cdot I_2$ (FIG. 12). Looking into that port from left to right, the energy-dissipating element can be considered the load $R_2$. As a result, it can be concluded that energy dissipated in $Z_1$ is the energy wasted in source impedance, and energy dissipated in $Z_T$ is the energy delivered to the load.

The following conditions can be used to maximize the power delivered to the load at sinusoidal steady state:

$$Z_1(j\omega) = Z_T(j\omega)^* \Rightarrow Z_1(j\omega) = \left[\frac{-(j\omega)^2 k^2 L_1 L_2}{Z_2(j\omega)}\right]^*,$$

which can be equivalent to the following two conditions:

$$|Z_1(j\omega)| = \left[\frac{-(j\omega)^2 k^2 L_1 L_2}{Z_2(j\omega)}\right] \Rightarrow \left|\frac{Z_1(j\omega)}{j\omega L_1}\right| = k^2 \left|\frac{j\omega L_2}{Z_2(j\omega)}\right|;$$

-continued $$\angle Z_1(j\omega) = -\angle\left[\frac{-(j\omega)^2 k^2 L_1 L_2}{Z_2(j\omega)}\right] \Rightarrow \angle Z_1(j\omega) = \angle Z_2(j\omega).$$

Figure 14A:
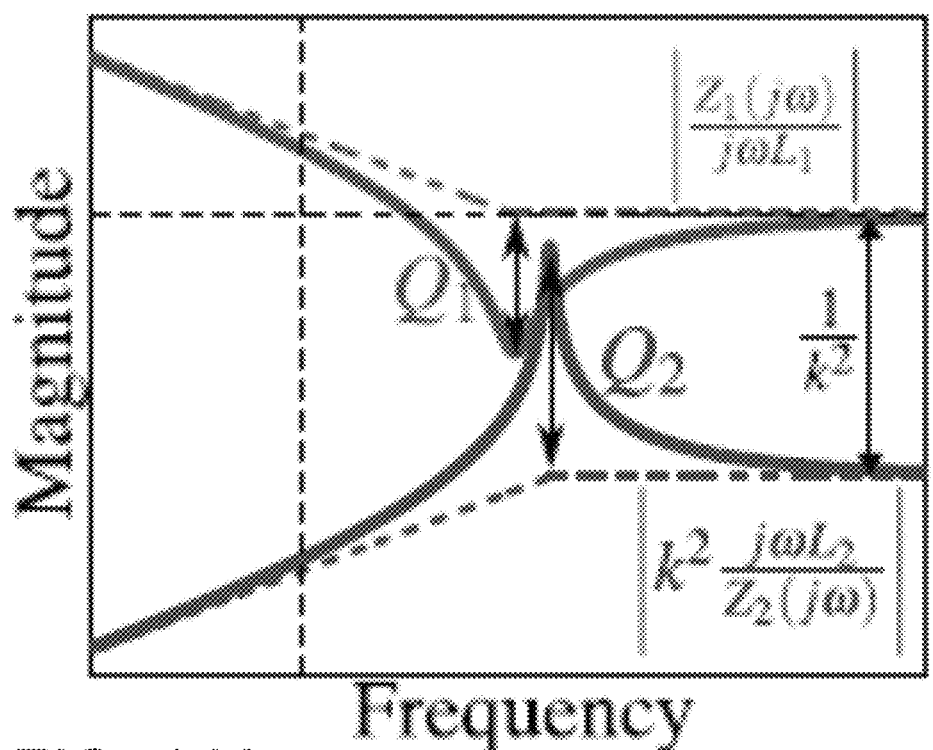
FIGS. 14A and 14B show graphical representations of maximum power transfer conditions of a wireless power transfer system in accordance with various embodiments of the invention.
Figure 14B:
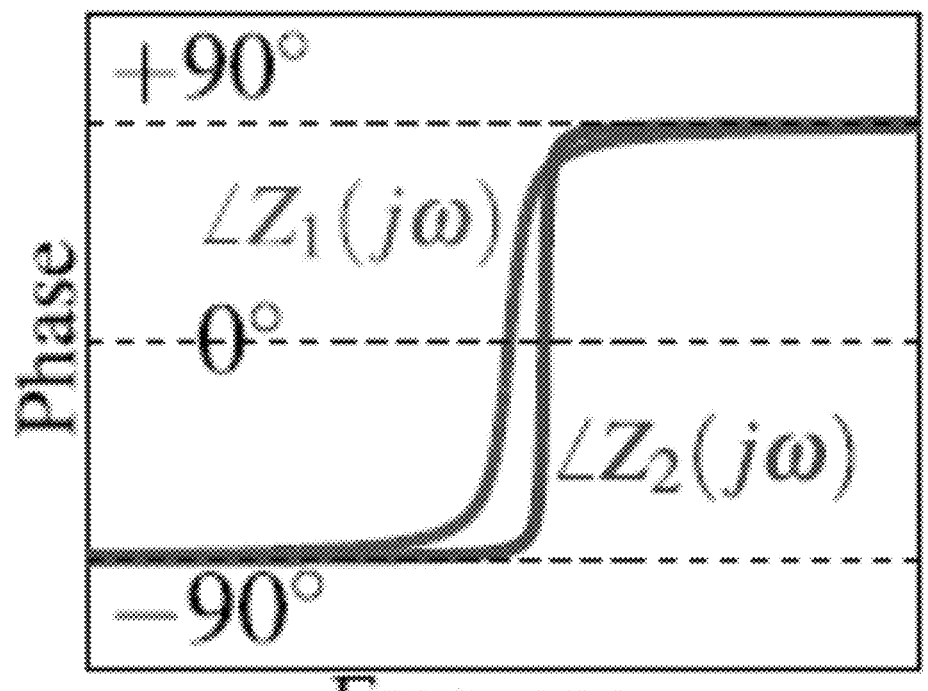

A graphical representation of the first condition is shown in FIG. 14A. As illustrated, the condition for maximum power transfer is manifested as two "Q-curves" intersecting on the graph. The second condition is shown in FIG. 14B. As illustrated, if the two "Q-curves" have different quality factor values, the point where $\angle Z_1(j\omega)$ and $\angle Z_2(j\omega)$ can be equal is at resonant frequency $\omega_0$. If $Z_1$ and $Z_2$ have the same quality factors, the two curves can completely coincide, meaning that the angles are equal to each other all the time. For instance, under the assumptions:

$$\omega_{res,1} = \frac{1}{\sqrt{L_1 C_1}} = \frac{1}{\sqrt{L_2 C_2}} = \omega_{res,2},$$

$$\text{and } Q_1 = \sqrt{\frac{L_1}{C_1}} \frac{1}{R_1} = \sqrt{\frac{L_1}{C_1}} \frac{1}{R_1} = Q_1 \gg 1,$$

$\angle Z_1(j\omega)=\angle Z_2(j\omega)$ is satisfied at all frequencies. To sum up, it can be desirable to set the two parts of the network to have the same resonant frequencies ($\omega_{res,1}=\omega_{res,2}$), the same quality factors ($Q_1=Q_2$), and as large quality factors as possible ($Q_1,Q_2 \gg 1$). A system meeting these requirements can transfer power in the following three different scenarios depending on the value of the coupling coefficient k in comparison to the critical coupling coefficient $k_c$, which can be defined as:

$$k_c \triangleq \sqrt{\frac{1}{Q_1 Q_2}} = \frac{1}{Q_2}, \text{ when } Q1 = Q2,$$

$$\text{and } \left|\frac{(\omega/\omega_{res})^2}{\left[1-(\omega/\omega_{res})^2\right]+(j\omega)/(\omega_{res}Q_{1,2})}\right| = \frac{1}{k} \Rightarrow \omega_1, \omega_2 \approx \frac{\omega_{res}}{\sqrt{1 \pm k}}.$$

When the system is under-coupled ($k<k_c$), the "Q-tips" never touch, and the system will typically not meet the maximum power transfer conditions. When the system is at critical-coupling ($k=k_c$), the "Q-tips" touch at the tips, and the system can meet the maximum power transfer conditions at resonant frequency. When the system is over-coupled ($k>k_c$), the "Q-tips" intersect at two points, and the system can meet the maximum power transfer conditions at the frequencies where the "Q-tips" intersect. The three power transfer scenarios are graphically depicted in FIGS. 15A-15C, respectively.

Figure 16A:
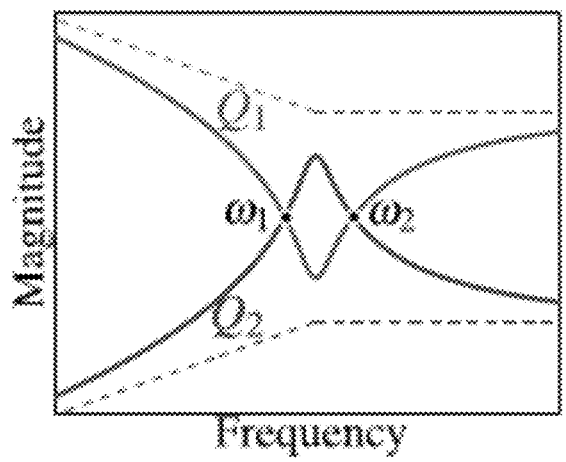
FIGS. 16A-16C show graphical representations of a shift in the optimal operation frequency due to asymmetry in accordance with various embodiments of the invention.
Figure 16B:
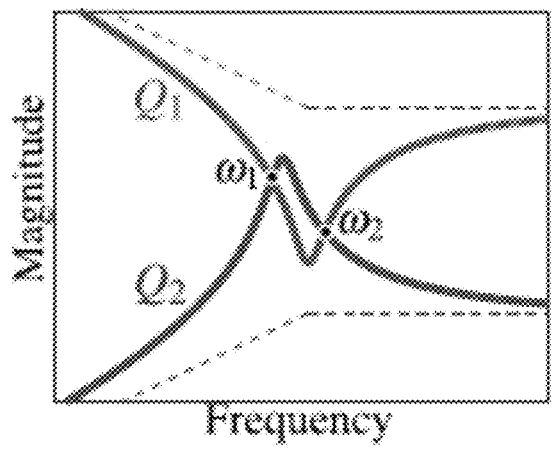
Figure 16C:
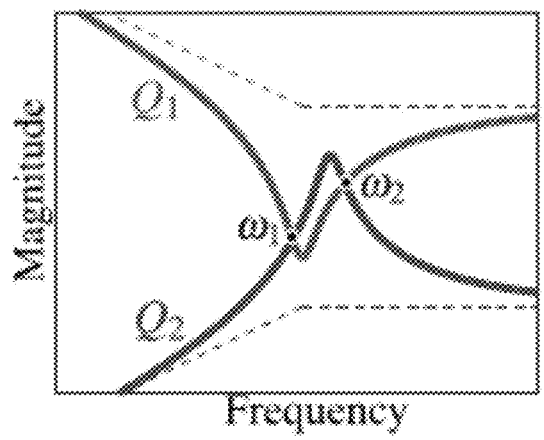

For $k>k_c$ (over-coupled), there are typically two frequencies ($\omega_1$, $\omega_2$) at which power transfer is ideal. A graphical representation of such conditions is shown in FIG. 16A. In this scenario, the system can eventually fall into one of the frequencies due to asymmetry. The frequency selection can depend on the values of $\omega_{res,1}$ and $\omega_{res,2}$. The two selection scenarios, $\omega_{res,2}<\omega_{res,1}$ and $\omega_{res,2}>\omega_{res,1}$, is graphically depicted in FIGS. 16B and 16C, respectively.

Simultaneous Wireless Data and Power Transmission Systems

Figure 17:
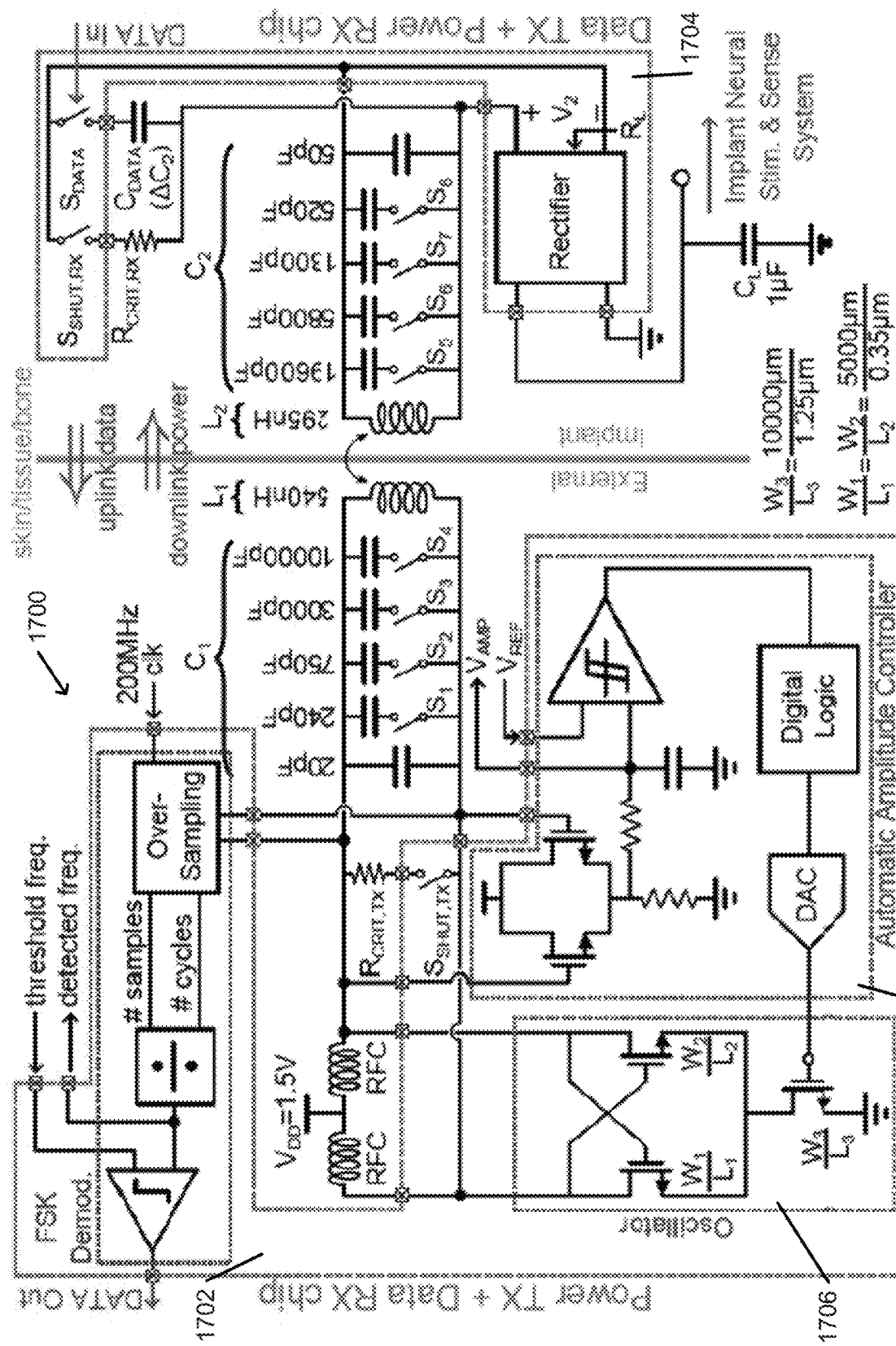
FIG. 17 shows an exemplary circuit for implementing a simultaneous data and power transmission system in accordance with an embodiment of the invention.

Biomedical implant systems configured for simultaneous data and power transmission in accordance with various embodiments of the invention can be implemented in many different ways. FIG. 17 shows an exemplary circuit for implementing a simultaneous data and power transmission system in accordance with an embodiment of the invention. As shown, the system 1700 includes an external transceiver 1702 for delivering power and receiving data. The system 1300 further includes an internal transceiver 1704 for receiving power and transmitting data. In the illustrative embodiment, the oscillator 1706 uses wide FETs to reduce the I²R loss during conduction. An AAC 1708 compares the rectified oscillator output with a DC reference and adjusts the tail current. The differential voltage across L₁ has a Class D-like waveform that exceeds the supply voltage (amplitude around 4 V). To expand the regulation range, the natural frequency $\omega_{res}$ of both resonators can be programmed with capacitor banks $C_1$ and $C_2$ through switches $S_1$-$S_8$. Therefore, when the implant current rises largely, such as at a transition from sensing to stimulation mode, the effective $R_L$ drops. In response, the switches lower $\omega_{res}$ to maintain the maximum regulation distance $d_c$.

Figure 18A:
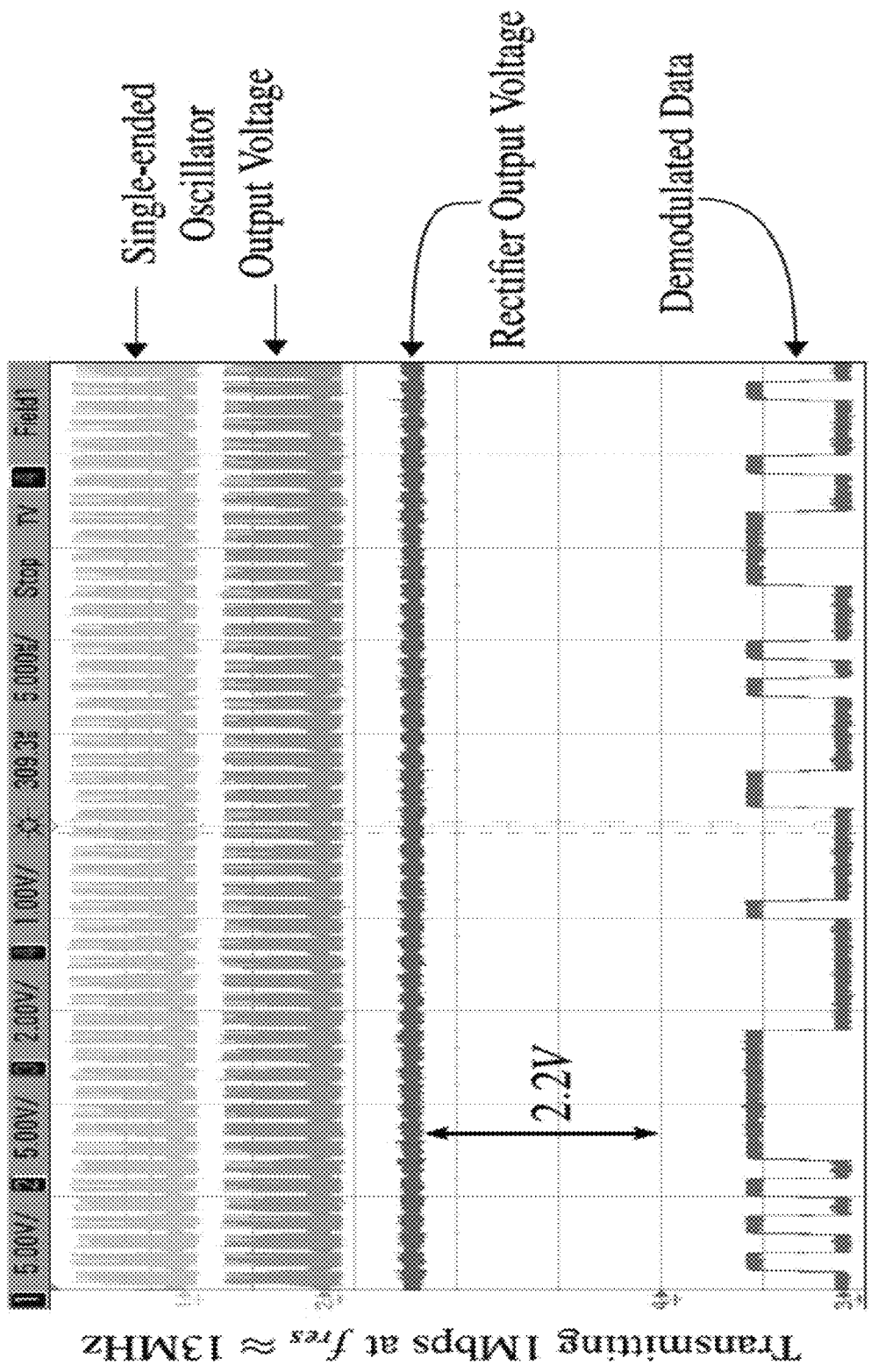
FIGS. 18A and 18B show measured operating waveforms at two oscillation frequencies in accordance with various embodiments of the invention.
Figure 18B:
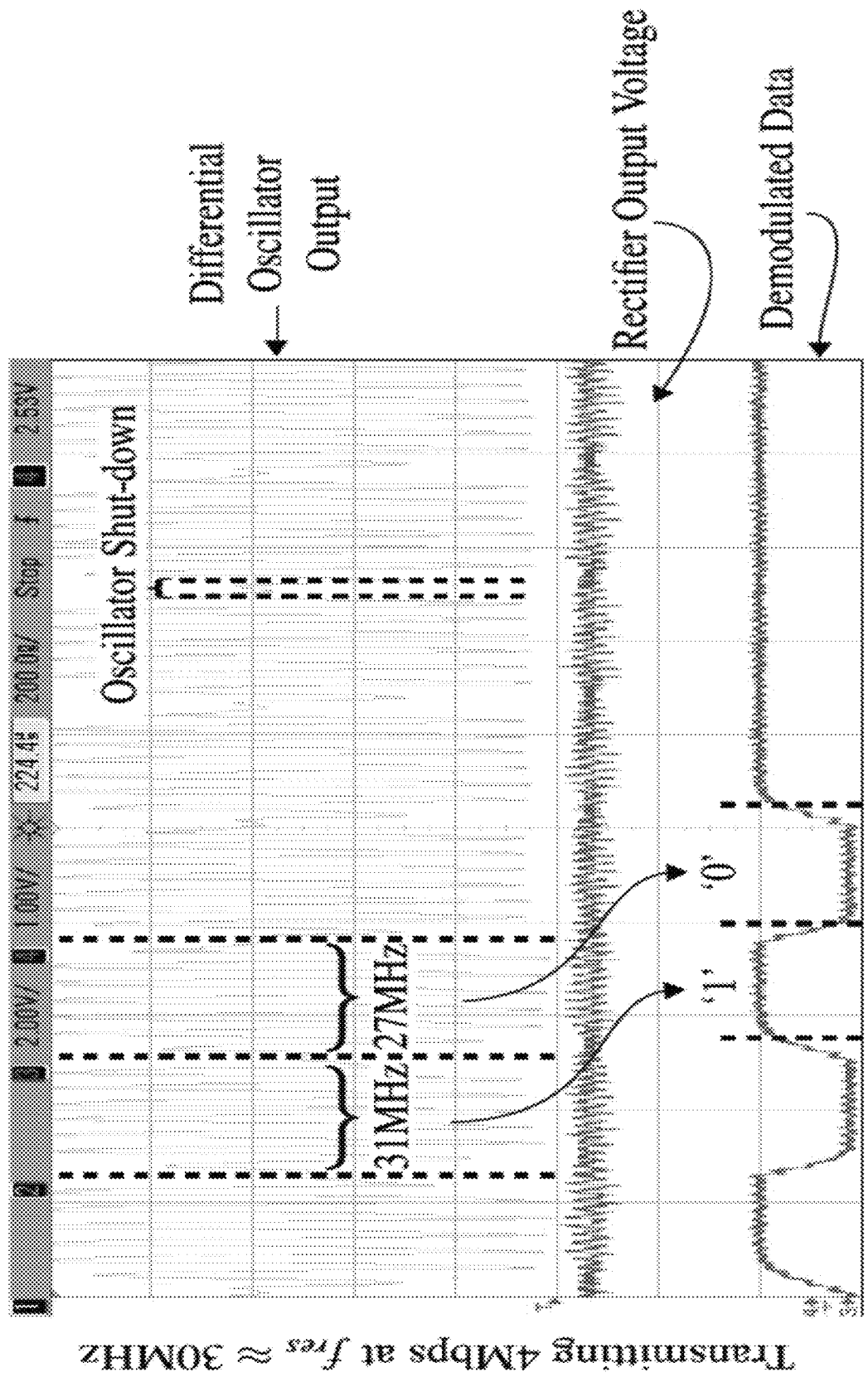

Wireless data can be transmitted from the implant to the primary side by toggling on-chip switch $S_{DATA}$. Before transmitting each bit, $S_{SHUT,TX}$ and $S_{SHUT,RX}$ can be closed to critically damp the two resonators and quench the original oscillation within one cycle. If the data bit transitions, $S_{DATA}$ can be toggled to force the oscillation to the other frequency. When $S_{SHUT,TX}$ and $S_{SHUT,RX}$ are released, the oscillation can build up quickly to reach steady-state at the new frequency. Diodes in the rectifier can be turned off during this process, but the large capacitor $C_L$ at the rectifier's output maintains steady load voltage with a droop less than 1 mV. In some embodiments, frequency switching takes ~10% of a bit period. In several embodiments, an all-digital FSK demodulator on the primary side over-samples the oscillation waveform at 200 MHz. A frequency estimate can be computed and compared with a threshold value to decide on the transmitted bit. FIGS. 18A and 18B show measured operating waveforms at two oscillation frequencies in accordance with an embodiment of the invention.

The external and implant subsystems can be integrated on two separate chips in 180 nm CMOS. In many embodiments, most power management blocks employ 350 nm I/O FETs. In some embodiments, $L_1$ and $L_2$ can be realized as 3-turn and 2-turn coils of 3 cm diameter wound with AWG18 copper wires. The discrete tuning capacitors can program resonance $f_{res}$ at one of 1.8, 3.39, 6.78, or 13.56 MHz. In a number of embodiments, oscillation can be tuned up to 30 MHz for highest data rate, but at the cost of more loss in the rectifier. In several embodiments, the drive can supply up to 93 mW to the implant, and the rectified DC output is around 2.1 V.

Figure 19:
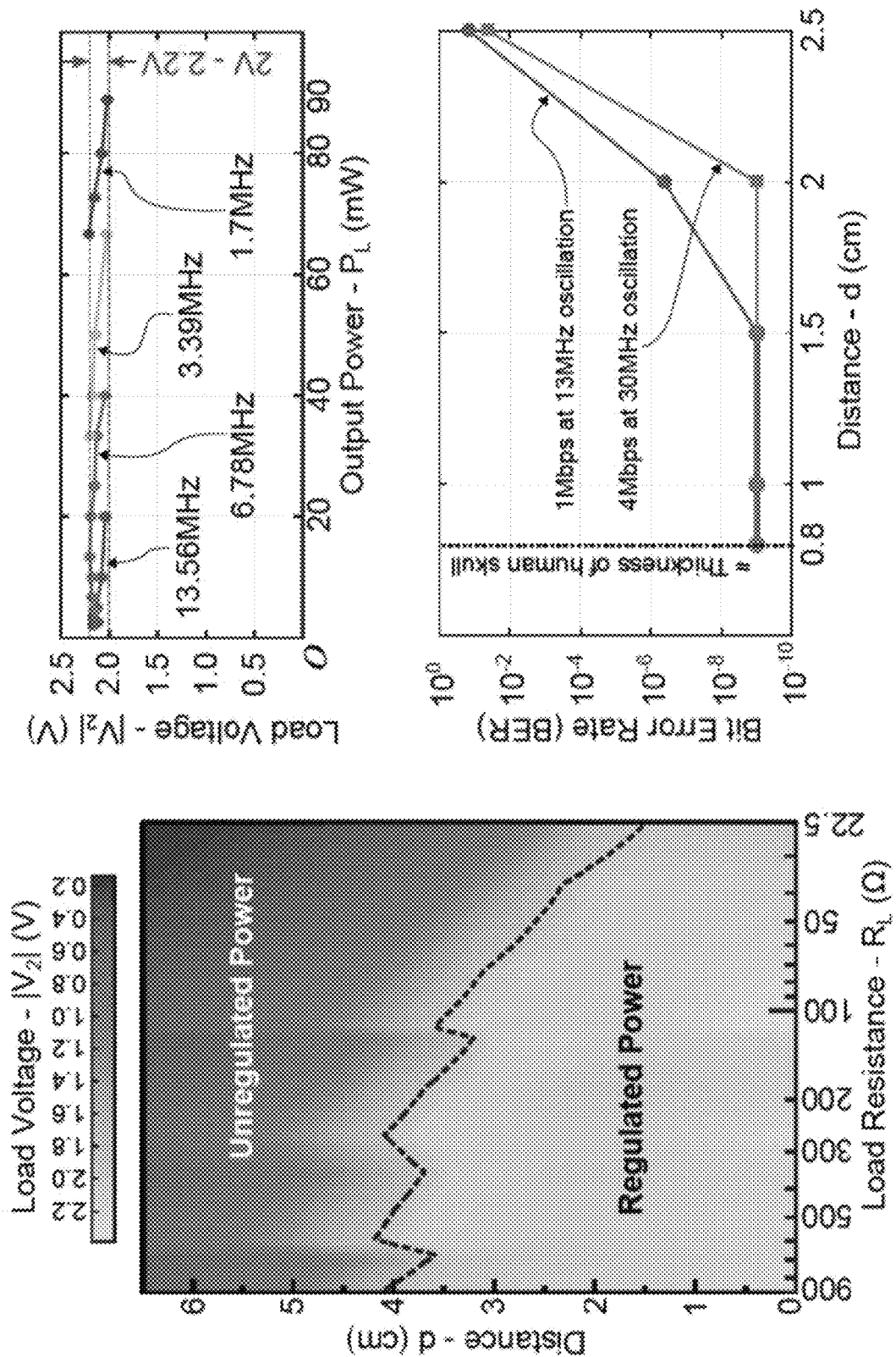
FIG. 19 shows the measured range of regulated power delivery over varying coil separation and effective load resistance in accordance with an embodiment of the invention.

FIG. 19 shows the measured range of regulated power delivery over varying coil separation and effective load resistance in accordance with an embodiment of the invention. Data rate can be limited by the bandwidth of the transfer function across the coupled resonators and also by the clock rate of the FSK demodulator. In many embodiments, the system can transmit 1 Mbps at $f_{res}$=13 MHz and 4 Mbps at $f_{res}$=30 MHz across coils as far apart as 2 cm, which is sufficient for a brain-machine interface. In further embodiments, a data rate of 5 Mbps can be achieved, limited to a distance of ~0.8 cm. Over all operating frequencies and at maximum transmitted power, the system complies with FCC § 15.209 radiation emission limits. FSK demodulation typically consumes about 7 mW of digital power. Modulator power in the implant can be set by the dynamic power to switch the gate capacitance of the FETs involved in modulation.

Although specific methods and systems for simultaneous near-field wireless power and data transmission are discussed above, many different systems can be implemented in accordance with many different embodiments of the invention. It is therefore to be understood that the present invention may be practiced in ways other than specifically described, without departing from the scope and spirit of the present invention. Thus, embodiments of the present invention should be considered in all respects as illustrative and not restrictive. Accordingly, the scope of the invention should be determined not by the embodiments illustrated, but by the appended claims and their equivalents.

What is claimed is:

1. A wireless inductive telemetry link comprising:
    an external transceiver comprising:
        a demodulation circuit comprising a counter and a finite state machine circuit for outputting an output data signal; and
    an internal transceiver comprising:
        a modulation circuit comprising a switch load capacitor for receiving an input data signal, wherein the switch capacitor is capable of receiving a data signal and modulating the data signal under a load-induced resonance-shift-keying modulation scheme;
    wherein the external transceiver is configured to transfer power to the internal transceiver while receiving data from the internal transceiver contemporaneously.

2. The wireless inductive telemetry link of claim 1, wherein:
    the external transceiver further comprises a first inductive coil;
    the internal transceiver further comprises a second inductive coil; and
    the external is configured to transfer power to the internal transceiver while receiving data from the internal transceiver contemporaneously using the first and second inductive coils.

3. The wireless inductive telemetry link of claim 2, wherein the load-induced resonance-shift-keying modulation scheme is implemented by using a switch capacitor to flip oscillation between two resonant frequencies, $\omega_L$ and $\omega_H$.

4. The wireless inductive telemetry link of claim 1, wherein the demodulation circuit further comprises an oscillator shut-down switch.

5. The wireless inductive telemetry link of claim 4, wherein the internal transceiver further comprises a large capacitor for supplying charge at oscillator shut-down.

6. The wireless inductive telemetry link of claim 1, wherein the external transceiver is configured to provide self-regulated power to the internal transceiver.

7. The wireless inductive telemetry link of claim 6, wherein the external transceiver is configured to provide self-regulated power to the internal transceiver within a coil separation $d_c$ range of 4.2 centimeters.

8. The wireless inductive telemetry link of claim 7, wherein the external transceiver is configured to provide self-regulated power to the internal transceiver within a coil separation $d_c$ range of 0.8 centimeters.

9. The wireless inductive telemetry link of claim 8, wherein the internal transceiver is configured to transmit data to the external transceiver at a data rate of 5 Mbps.

10. The wireless inductive telemetry link of claim 9, wherein the power transfer efficiency is above 35%.

11. A method for simultaneous power and data transmission, the method comprising:

transmitting data from an internal transceiver to an external transceiver, wherein:
  the external transceiver comprises a demodulation circuit comprising a counter and a finite state machine circuit for outputting an output data signal; and
  the internal transceiver comprises a modulation circuit comprising a switch load capacitor for receiving an input data signal, wherein the switch capacitor is capable of receiving a data signal and modulating the data signal under a load-induced resonance-shift-keying modulation scheme; and
transferring power from the external transceiver to the internal transceiver contemporaneously with the transmittal of data from the internal transceiver.

12. The method claim 11, wherein:
the external transceiver further comprises a first inductive coil;
the internal transceiver further comprises a second inductive coil; and
the transmission of data and transferal of power are performed through the first and second inductive coils.

13. The method of claim 12, wherein the load-induced resonance-shift-keying modulation scheme is implemented by using a switch capacitor to flip oscillation between two resonant frequencies, $\omega_L$ and $\omega_H$.

14. The method of claim 11, wherein the demodulation circuit further comprises an oscillator shut-down switch.

15. The method of claim 14, wherein the internal transceiver further comprises a large capacitor for supplying charge at oscillator shut-down.

16. The method of claim 11, wherein the external transceiver is configured to provide self-regulated power to the internal transceiver.

17. The method of claim 16, wherein the external transceiver is configured to provide self-regulated power to the internal transceiver within a coil separation $d_c$ range of 4.2 centimeters.

18. The method of claim 17, wherein the external transceiver is configured to provide self-regulated power to the internal transceiver within a coil separation $d_c$ range of 0.8 centimeters.

19. The method of claim 18, wherein the data is transmitted to the external transceiver at a data rate of 5 Mbps.

20. The method of claim 19, wherein the power is transferred with a power transfer efficiency above 35%.

* * * * *